United States Patent
Wei et al.

(10) Patent No.: US 11,498,973 B2
(45) Date of Patent: *Nov. 15, 2022

(54) BCMA-TARGETED CHIMERIC ANTIGEN RECEPTOR AS WELL AS PREPARATION METHOD THEREFOR AND APPLICATION THEREOF

(71) Applicant: CELLULAR BIOMEDICINE GROUP HK LIMITED, Hong Kong (CN)

(72) Inventors: Yutian Wei, Hong Kong (CN); Lin Zhu, Hong Kong (CN); Yanfeng Li, Hong Kong (CN); Yihong Yao, Hong Kong (CN); Xin Yao, Hong Kong (CN); Jiaqi Huang, Hong Kong (CN); Li Zhang, Hong Kong (CN); Shigui Zhu, Hong Kong (CN); Xiaoteng Lv, Hong Kong (CN)

(73) Assignee: CELLULAR BIOMEDICINE GROUP HK LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/476,661

(22) Filed: Sep. 16, 2021

(65) Prior Publication Data
US 2021/0403590 A1  Dec. 30, 2021

Related U.S. Application Data

(63) Continuation of application No. 16/881,668, filed on May 22, 2020, now Pat. No. 11,142,581, which is a continuation-in-part of application No. PCT/CN2019/081064, filed on Apr. 2, 2019.

(30) Foreign Application Priority Data

Apr. 12, 2018  (CN) .......................... 201810326346.9

(51) Int. Cl.
*A61K 35/17* (2015.01)
*A61P 35/00* (2006.01)
*C07K 16/28* (2006.01)
*C07K 14/725* (2006.01)
*C12N 5/0783* (2010.01)

(52) U.S. Cl.
CPC .......... *C07K 16/2878* (2013.01); *A61K 35/17* (2013.01); *A61P 35/00* (2018.01); *C07K 14/7051* (2013.01); *C12N 5/0636* (2013.01); *C07K 2319/02* (2013.01); *C07K 2319/03* (2013.01)

(58) Field of Classification Search
None
See application file for complete search history.

(56) References Cited

U.S. PATENT DOCUMENTS

2015/0051266 A1  2/2015  Kochenderfer

FOREIGN PATENT DOCUMENTS

| | | |
|---|---|---|
| CN | 104114578 A | 10/2014 |
| CN | 104379179 A | 2/2015 |
| CN | 105384825 A | 3/2016 |
| CN | 106795217 A | 5/2017 |
| CN | 107827989 A | 3/2018 |
| WO | 2016/014789 A2 | 1/2016 |
| WO | 2017/072716 A1 | 5/2017 |
| WO | 2017/172981 A2 | 10/2017 |
| WO | 2017/210617 A2 | 12/2017 |

OTHER PUBLICATIONS

Chimeric antigen receptor T cell—Wikipedia pp. 1-9; downloaded Mar. 4, 2022.*

* cited by examiner

*Primary Examiner* — Maria G Leavitt
(74) *Attorney, Agent, or Firm* — Leason Ellis LLP

(57) ABSTRACT

The present invention provides a BCMA-targeted chimeric antigen receptor (CAR) as well as a preparation method therefor and an application thereof. Specifically, the present invention provides the BCMA-targeted CAR, which comprises a BCMA-targeted scFv, a hinge region, a transmembrane region, and an intracellular signal structure domain. The present invention provides a nucleic acid molecule for coding the CAR and a corresponding expression vector as well as CAR-T cells and application thereof. The CAR of the present invention targets BCMA-positive cells, and can be used for treating BCMA-positive B-cell lymphoma, multiple myeloma and plasma cell leukemia.

4 Claims, 13 Drawing Sheets

Specification includes a Sequence Listing.

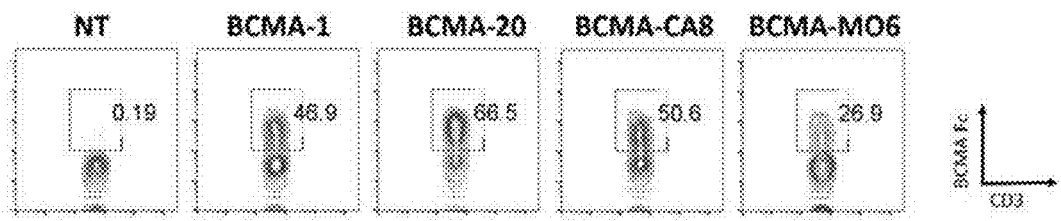
FIG. 2
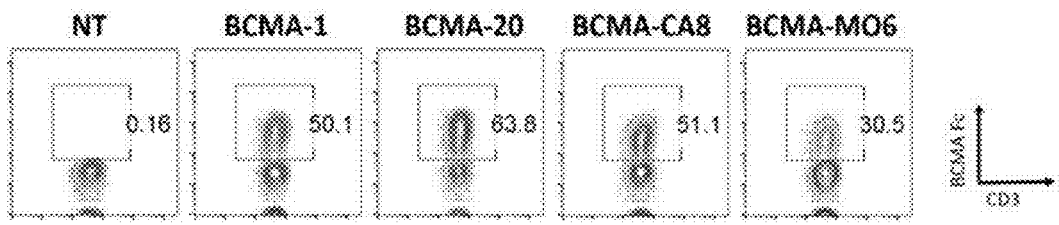
FIG. 3A
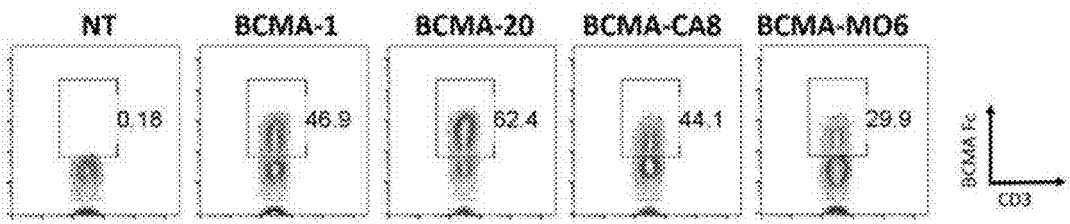
FIG. 3B
FIG. 3C

*Blood myeloma marker: serum M protein/ free light chains (FLC)

Z0203-00701C001

BCMA-TARGETED CHIMERIC ANTIGEN RECEPTOR AS WELL AS PREPARATION METHOD THEREFOR AND APPLICATION THEREOF

CROSS-REFERENCE TO RELATED APPLICATIONS

This application is a continuation of U.S. Patent Application No. 16/881,668 filed on May 22, 2020, now U.S. Pat. No. 11,142,581, which is a continuation-in-part of PCT Application No. PCT/CN2019/081064 filed on Apr. 2, 2019, which claims the benefit of Chinese Patent Application No. 201810326346.9 (filed on Apr. 12, 2018). The entire contents of all of these applications are incorporated by reference in their entirety.

TECHNICAL FIELD

The invention relates to the field of bio-medicine, and more particularly to a BCMA targeting chimeric antigen receptor as well as preparation method and application thereof.

BACKGROUND TECHNIQUE

BCMA is a B cell maturation antigen, also known as CD269 or TNFRSF17, and is a member of the tumor necrosis factor receptor superfamily Its ligands are B cell activating factor (BAFF) and a proliferation-induced ligand (APRIL).

Binding of BCMA to BAFF and APRIL activates NF-kB and induces up-regulation of anti-apoptotic Bcl-2 members such as Bcl-xL or Bcl-2 and Mcl-1. The interaction between BCMA and its ligands regulates humoral immunity as well as the growth and differentiation of B cells from different aspects to maintain a stable and balanced environment in the human body.

The expression of BCMA is restricted to B cell lines. It is expressed on plasmablasts, plasma cells and a portion of mature B cells, and increased at the differentiation of terminal B cells. While in most B cells, such as naive B cells, memory B cells and B cell germinal centers and other organs, BCMA is not expressed. It has been reported that the expression of BCMA is important for long-lived, fixed plasma cells in the bone marrow. Therefore, plasma cells in the bone marrow are reduced in BCMA-deficient mice, but plasma cell level in the spleen is not affected. Mature B cells can normally differentiate into plasma cells in BCMA knockout mice. The BCMA knockout mice looked normal and seemed healthy, and the number of B cells was normal, but the plasma cells could not survive for a long time.

BCMA is also highly expressed in malignant plasma cells, such as multiple myeloma and plasma cell leukemia. BCMA is also detected in HRS cells of patients with Hodgkin's lymphoma. In America, malignant tumors of blood system account for about 10% of all malignant tumors, and myeloma accounts for 15% of all malignant hematological tumors. According to the literature, the expression of BCMA is associated with progression of multiple myeloma disease. The BCMA gene is highly expressed in myeloma samples, but is low expressed in chronic lymphocytic leukemia, acute lymphocytic leukemia, and acute T-cell lymphocytic leukemia. B cell lymphomas were significantly increased in a mouse model overexpressing BCMA ligands BAFF and APRIL. Ligands that bind to BCMA have been shown to regulate the growth and survival of multiple myeloma cells expressing BCMA. The combination of BCMA with BAFF and APRIL can make malignant plasma cells survive. Therefore, loss of tumor cells expressing BCMA and distribution of the interaction between BCMA ligand and receptor can improve outcome in the treatment of multiple myeloma or other BCMA positive B cell lines malignant lymphoma.

Multiple myeloma, also known as plasmacytoma or Keller's disease, is a malignant tumor of the refractory B cell line, characterized by abnormal proliferation of plasma cells. Plasma cells are a type of leukocyte that is responsible for production of antibodies. According to data released by the National Cancer Institute in 2017, myeloma accounts for 1.8% of all tumor cases, with a mortality rate of 2.1%. The statistical results of 2010-2014 show that the incidence rate is about 6.6 in 100,000 per year and the mortality rate is about 50%. Multiple myeloma is a middle-aged disease. The median age of onset in Europe and the United States is 68 years old. There are more males than females. The peak age of onset in China is 55-65 years old, and the ratio of male to female is 2.35:1. There is no confirmed epidemiological data on multiple myeloma in China. It is generally estimated that the incidence rate is similar to that in surrounding southeast Asia and Japan, about one in 100,000. Traditional treatments for multiple myeloma include chemotherapy and hematopoietic stem cell transplantation, but these methods have a high recurrence rate. Bortezomib (PS-341) is first proteasome inhibitor, which is approved by the FDA in 2003 for the treatment of relapsed refractory multiple myeloma, either alone or in combination with existing medications. The results were gratifying. The drug was also marketed in China in 2005 and has become one of the options for the treatment of multiple myeloma with thalidomide and dexamethasone. The treatment of multiple myeloma is usually combined. However, if multiple drugs are used at the same time, there are also negative effects of costly and cumulative side effects. There is still a clinical need to develop new methods for the treatment of multiple myeloma.

Recently, immunotherapy, especially adoptive T-cell therapy, has shown strong efficacy and bright prospects in clinical trials for the treatment of malignant tumors of the blood system. T cells can be genetically modified to express a chimeric antigen receptor (CAR), which includes an antigen recognition portion and a T cell activation region. Using the antigen binding properties of monoclonal antibodies, CAR can redirect the specificity and reactivity of T cell and target in a non-MHC restricted manner. This non-MHC restricted antigen recognition allows CAR-expressing T cells to recognize antigen without antigen processing, thus avoiding a major mechanism of tumor escape. In addition, CAR does not produce dimers with alpha chain and beta chain of the endogenous TCR.

At present, two chimeric antigen receptor T cell therapy (CAR-T) products targeting CD19 have been approved for the treatment of acute lymphoblastic leukemia in children and young adult patients and adult second-line or multi-line system therapy of recurrent or refractory large B-cell lymphoma. However, CD19 is rarely expressed in malignant plasma cells of multiple myeloma. There is an urgent need in the art to develop a CAR-T product that targets BCMA for the treatment of multiple myeloma.

SUMMARY OF THE INVENTION

It is an object of the present invention to provide a BCMA targeted chimeric antigen receptor as well as preparation method and application thereof.

Specifically, it is an object of the present invention to provide a sequence of BCMA targeted chimeric antigen receptor as well as preparation method and activity identification of a modified T cell (CART-BCMA) thereof.

The present invention provides a chimeric antigen receptor structure for use in the treatment of BCMA positive B cell lymphoma.

In a first aspect of the invention, it provides a chimeric antigen receptor (CAR) (sequence), and its antigen binding domain is an antibody single chain variable region sequence that targets extracellular region of BCMA.

In another preferred embodiment, the antigen binding domain is an antibody single chain variable region sequence that targets amino acid residues at positions 24 to 41 of the BCMA sequence.

In another preferred embodiment, the NCBI accession number of the BCMA sequence is AY684975.1.

In another preferred embodiment, the structure of the antigen binding domain is shown in formula I as below:

wherein $V_H$ is an antibody heavy chain variable region; $V_L$ is an antibody light chain variable region; and "-" is a linker peptide or a peptide bond;

and, the amino acid sequence of $V_L$ is as shown in SEQ ID NO: 1, and the amino acid sequence of $V_H$ is as shown in SEQ ID NO: 2;

or, the amino acid sequence of $V_L$ is as shown in SEQ ID NO: 3, and the amino acid sequence of $V_H$ is as shown in SEQ ID NO: 4;

or, the amino acid sequence of $V_L$ is as shown in SEQ ID NO: 5, and the amino acid sequence of $V_H$ is as shown in SEQ ID NO: 6.

In another preferred embodiment, the amino acid sequence of the linker peptide is as shown in SEQ ID NO: 10 or SEQ ID NO: 11.

In another preferred embodiment, the antibody single chain variable region comprises a human, mouse, human-mouse chimeric antibody single chain variable region.

In another preferred embodiment, the structure of the chimeric antigen receptor is shown in formula II as below:

wherein,
S is an optional signal peptide;
H is a hinge region;
TM is a transmembrane domain;
C is a co-stimulatory signaling molecule;
CD3ζ is a cytoplasmic signaling sequence derived from CD3ζ;
$V_H$ and $V_L$ are as described above.

In another preferred embodiment, the S is a signal peptide of a protein selected from the group consisting of CD8, CD28, GM-CSF, CD4, CD137, or a combination thereof.

In another preferred embodiment, the S is a signal peptide derived from CD8.

In another preferred embodiment, the amino acid sequence of S is as shown in SEQ ID NO: 9.

In another preferred embodiment, the H is a hinge region of a protein selected from the group consisting of CD8, CD28, CD137, or a combination thereof.

In another preferred embodiment, the H is a hinge region derived from CD8.

In another preferred embodiment, the amino acid sequence of H is as shown in SEQ ID NO: 12.

In another preferred embodiment, the TM is a transmembrane region of a protein selected from the group consisting of CD28, CD3ε, CD45, CD4, CD5, CD8, CD9, CD16, CD22, CD33, CD37, CD64, CD80, CD86, CD134, CD137, CD154, or a combination thereof.

In another preferred embodiment, the TM is a transmembrane region derived from CD8.

In another preferred embodiment, the sequence of TM is as shown in SEQ ID NO: 13.

In another preferred embodiment, the C is a co-stimulatory signaling molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, or a combination thereof.

In another preferred embodiment, C is a co-stimulatory signaling molecule derived from 4-1BB.

In another preferred embodiment, the amino acid sequence of C is as shown in SEQ ID NO: 14.

In another preferred embodiment, the amino acid sequence of CD3ζ is as shown in SEQ ID NO: 15.

In a second aspect of the invention, it provides a nucleic acid molecule, encoding the chimeric antigen receptor (CAR) of the first aspect of the invention.

In another preferred embodiment, the nucleic acid molecule is isolated.

In a third aspect of the invention, it provides a vector, comprising the nucleic acid molecule of the second aspect of the invention.

In another preferred embodiment, the vector is selected from the group consisting of DNA, RNA, plasmid, lentiviral vector, adenoviral vector, retroviral vector, transposon, or a combination thereof.

In another preferred embodiment, the vector is a lentiviral vector.

In a fourth aspect of the invention, it provides a host cell, comprising the vector of the third aspect of the invention or having the exogenous nucleic acid molecule of the second aspect of the invention integrated into the chromosome or expressing the CAR of the first aspect of the invention.

In another preferred embodiment, the cell is an isolated cell, and/or the cell is a genetically engineered cell.

In another preferred embodiment, the cell is a mammalian cell.

In another preferred embodiment, the cell is a T cell.

In a fifth aspect of the invention, it provides a method for preparing a CAR-T cell expressing the CAR of the first aspect of the invention, and the method comprises the steps of:

transducing the nucleic acid molecule of the second aspect of the invention or the vector of the third aspect of the invention into a T cell, thereby obtaining the CAR-T cell.

In a sixth aspect of the invention, it provides a preparation, comprising the chimeric antigen receptor of the first aspect of the invention, the nucleic acid molecule of the second aspect of the invention, the vector of the third aspect of the invention, or the cell of the fourth aspect of the invention, and a pharmaceutically acceptable carrier, diluent or excipient.

In another preferred embodiment, the preparation is a liquid preparation.

In another preferred embodiment, the dosage form of the preparation is injection.

In another preferred embodiment, the concentration of the CAR-T cells in the preparation is $1 \times 10^3$–$1 \times 10^8$ cells/ml, preferably $1 \times 10^4$–$1 \times 10^7$ cells/ml.

In a seventh aspect of the invention, it provides the use of the chimeric antigen receptor of the first aspect of the invention, the nucleic acid molecule of the second aspect of the invention, the vector of the third aspect of the invention, or the cell of the fourth aspect of the invention, for the preparation of a medicine or a preparation for preventing and/or treating tumor or cancer.

In another preferred embodiment, the tumor is selected from the group consisting of a hematological tumor, a solid tumor, or a combination thereof.

In another preferred embodiment, the blood tumor is selected from the group consisting of acute myeloid leukemia (AML), multiple myeloma (MM), chronic lymphocytic leukemia (CLL), acute lymphoblastic leukemia (ALL), diffuse large B cell lymphoma (DLBCL), or a combination thereof.

In another preferred embodiment, the solid tumor is selected from the group consisting of gastric cancer, peritoneal metastasis of gastric cancer, liver cancer, leukemia, renal cancer, lung cancer, small intestine cancer, bone cancer, prostate cancer, colorectal cancer, breast cancer, large intestine cancer, cervical cancer, ovarian cancer, lymphoma, nasopharyngeal carcinoma, adrenal tumor, bladder tumor, non-small cell lung cancer (NSCLC), glioma, endometrial cancer, or a combination thereof.

In another preferred embodiment, the tumor is a BCMA positive tumor, preferably a BCMA positive B cell lymphoma, multiple myeloma, or plasma cell leukemia.

In an eighth aspect of the invention, it provides a kit for the preparation of the cell of the fourth aspect of the invention, the kit comprises a container, and the nucleic acid molecule of the second aspect of the invention or the vector of the third aspect of the invention is located in the container.

In a ninth aspect of the invention, it provides a use of the cell of the fourth aspect of the invention, or the preparation of the sixth aspect of the invention for the prevention and/or treatment of cancer or tumor.

In a tenth aspect of the invention, it provides a method of treating a disease comprising administering an appropriate amount of the cell of the fourth aspect of the invention, or the preparation of the sixth aspect of the invention, to a subject in need of treatment.

In another preferred embodiment, the disease is cancer or tumor.

It is to be understood that the various technical features of the present invention mentioned above and the various technical features specifically described hereinafter (as in the Examples) may be combined with each other within the scope of the present invention to constitute a new or preferred technical solution, which needs not be described one by one, due to space limitations.

DESCRIPTION OF DRAWINGS

FIG. 1A shows detection of transfection efficiency of engineered T cell with chimeric antigen receptors targeting BCMA. The expression level of the CAR gene-encoded protein on the surface of the T cell membrane in CAR-BCMA cells cultured on day 6 was identified by Fc fragment staining method of recombinant human BCMA protein. 1*$10^5$ of CART-BCMA cells cultured on day 10 were cultured respectively with BCMA-positive K562-BCMA-B9 tumor cell line, MM.1S and RPMI8226 tumor cell lines naturally expressing BCMA, and BCMA-negative K562 tumor cell line, or without tumor cells, in 200 µl GT-551 medium for 18 h at a ratio of 1:1. Then the expression level of CD137 on the surface of T cell membrane (FIG. 1B) and the secretion level of IFNγ in the culture supernatant was detected respectively (FIG. 1C).

FIG. 2 shows structure of chimeric antigen receptor targeting BCMA. The structure of CAR includes a leader sequence, an antigen recognition sequence, a linker region, a transmembrane region, a co-stimulatory factor signal region, and a CD3ζ signaling region.

FIGS. 3A, 3B, and 3C show detection of transfection efficiency of engineered T cell with chimeric antigen receptors targeting BCMA. The expression levels of the CAR gene-encoded protein on the surface of the T cell membrane in CAR-BCMA cells cultured on day 7 (FIG. 3A) day 21 (FIG. 3B) and day 29 (FIG. 3C) were identified by Fc fragment staining method of recombinant human BCMA protein.

FIG. 6A shows ratio of CART positive cells in the analyzed samples, wherein NT and BCMA-M06 were calculated at 60%. 1×$10^4$ CFSE-labeled BCMA-negative (NH929) or BCMA-positive (NH929-BCMA, MM.1S) tumor cell lines were co-cultured respectively with corresponding T cells in 100 µl of GT-551 medium for 4 h at a ratio as shown in the figure. The proportion of PI-positive cells in CFSE-positive cells was analyzed by flow cytometry after staining with 100 µl of 25% PI dye for 15 min. FIG. 6B shows the statistical analysis of PI positive cells in the corresponding co-culture samples.

FIG. 7A shows that single injection of CART-BCMA-1 and CART-BCMA-20 through tail vein can effectively inhibit the growth of human myeloma RPMI-8226 cells. FIG. 7B shows that CART-BCMA-1 and CART-BCMA-20 can significantly prolong the survival of tumor-bearing mice with human myeloma RPMI-8226 cells.

MODES FOR CARRYING OUT THE PRESENT INVENTION

Figure 1A:
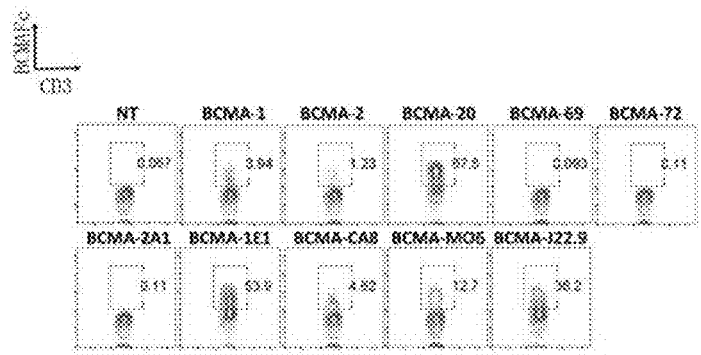
FIGS. 1A, 1B, and 1C show screening result of CART-BCMA comparative examples.

After extensive and intensive studies and screening, the inventors have obtained a chimeric antigen receptor targeting BCMA antigen for the first time. Specifically, the present invention obtains a chimeric antigen receptor structure targeting BCMA based on four monoclonal antibody sequences of BCMA-1, BCMA-20, BCMA-CA8, and BCMA-MO6, and completes the analysis and identification of the expression level in primary T cells, in vitro activation ability and tumor cell killing efficacy of these chimeric antigen receptors. Studies have shown that the chimeric antigen receptors of the present invention target BCMA positive cells and can be used to treat BCMA positive B cell lymphoma, multiple myeloma, plasma cell leukemia or other diseases.

Specifically, the present invention identifies the correlation between the expression time and the expression intensity of different CAR structures on the surface of the cell membrane after virus infection, and further identifies the difference in expression of different CAR structural proteins. This finding suggests that different CAR structures exist a difference in the expression level of CAR protein on the membrane surface and the persistence of CART in vivo activity under same infection condition. After extensive screening, the CAR structure of the present invention was obtained. The results show that the protein encoded by the CAR structure of the present invention can be fully expressed and membrane-localized.

In the present invention, the preparation process of CAR-modified T cell targeting BCMA antigen is improved. Primarily, GT-551 serum-free medium supplemented with 1% human albumin was selected to culture lymphocytes in vitro.

Term

To make the disclosure easier to understand, some terms are firstly defined. As used in this application, unless expressly stated otherwise herein, each of the following terms shall have the meanings given below. Other definitions are set forth throughout the application.

The term "about" may refer to a value or composition within an acceptable error range for a particular value or composition as determined by those skilled in the art, which will depend in part on how the value or composition is measured or determined.

The term "administering" refers to the physical introduction of a product of the invention into a subject using any one of various methods and delivery systems known to those skilled in the art, including intravenous, intramuscular, subcutaneous, intraperitoneal, spinal or other parenteral administration, such as by injection or infusion.

The term "antibody" (Ab) may include, but is not limited to, an immunoglobulin that specifically binds an antigen and contains at least two heavy (H) chains and two light (L) chains linked by disulfide bonds, or an antigen binding parts thereof. Each H chain contains a heavy chain variable region (abbreviated herein as VH) and a heavy chain constant region. The heavy chain constant region contains three constant domains, CH1, CH2, and CH3. Each light chain contains a light chain variable region (abbreviated herein as VL) and a light chain constant region. The light chain constant region contains a constant domain CL. The VH and VL regions can be further subdivided into hypervariable regions called complementarity determining regions (CDR), which are interspersed within more conservative regions called framework regions (FR). Each VH and VL contains three CDRs and four FRs, which are arranged from amino terminal to carboxy terminal in the following order: FR1, CDR1, FR2, CDR2, FR3, CDR3, FR4. The variable regions of the heavy and light chains contain a binding domain that interacts with an antigen.

Chimeric Antigen Receptor (CAR)

The chimeric antigen receptor (CAR) of the invention comprises an extracellular domain, a transmembrane domain, and an intracellular domain. The extracellular domain comprises a target-specific binding element (also known as an antigen binding domain). The intracellular domain includes a co-stimulatory signaling region and a chain. The co-stimulatory signaling region refers to a part of the intracellular domain that includes a co-stimulatory molecule. The co-stimulatory molecule is a cell surface molecule required for efficient response of lymphocytes to antigens, rather than a antigen receptor or its ligand.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that plays a role of linking the transmembrane domain to the extracellular domain or the cytoplasmic domain in a polypeptide chain. The linker may comprise 0-300 amino acids, preferably 2-100 amino acids and most preferably 3-50 amino acids.

In a preferred embodiment of the invention, the extracellular domain of the CAR provided by the invention comprises an antigen binding domain targeting BCMA. When the CAR of the present invention is expressed in T cell, antigen recognition can be performed based on antigen binding specificity. When the CAR binds to its associated antigen, it affects tumor cell, causing tumor cell to fail to grow, to death or to be affected otherwise, causing the patient's tumor burden to shrink or eliminate. The antigen binding domain is preferably fused to the intracellular domain from one or more of the co-stimulatory molecule and the ζ chain. Preferably, the antigen binding domain is fused with an intracellular domain of a combination of a 4-1BB signaling domain and a CD3ζ signaling domain.

As used herein, the "antigen binding domain" and "single-chain antibody fragment" refer to a Fab fragment, a Fab' fragment, a F(ab')$_2$ fragment, or a single Fv fragment that has antigen-binding activity. The Fv antibody contains the heavy chain variable region and the light chain variable region of the antibody, but has no constant region. The Fv antibody has the smallest antibody fragment with all antigen-binding sites. Generally, Fv antibodies also include a polypeptide linker between the VH and VL domains, and can form the structure required for antigen binding. The antigen binding domain is usually a scFv (single-chain variable fragment). The size of scFv is typically ⅙ of a complete antibody. The single-chain antibody is preferably an amino acid chain sequence encoded by a nucleotide chain. As a preferred mode of the present invention, the scFv comprises an antibody which specifically recognizes the extracellular region of BCMA, particularly an antibody which specifically recognizes amino acid residues at positions 24 to 41 of the BCMA sequence, preferably a single chain antibody.

As for the hinge region and the transmembrane region (transmembrane domain), the CAR can be designed to comprise a transmembrane domain fused to the extracellular domain of the CAR. In one embodiment, a transmembrane domain that is naturally associated with one of the domains in the CAR is used. In some embodiments, transmembrane domains may be selected or modified by amino acid substitutions to avoid binding such domains to the transmembrane domain of the same or different surface membrane proteins, thereby minimizing the interaction with other members of the receptor complexes.

The intracellular domain in the CAR of the invention comprises the signaling domain of 4-1BB and the signaling domain of CD3ζ.

Preferably, the CAR structure of the present invention comprises a signal peptide, an antigen recognition sequence (antigen-binding domain), a linker region, a transmembrane region, a co-stimulatory factor signal region, and a CD3zeta signaling region (ζ chain portion).

The order of connection is as follows:

[CD8 S]-[VL-Linker-VH]-[hinge-CD8TM]-[4-1BB]-[CD3zeta]

Specifically, the sequence selected in the present invention is as follows:

(1) The signal peptide is a signal peptide sequence derived from CD8:

```
                                           (SEQ ID NO: 9)
            MALPVTALLLPLALLLHAARP
```

(2) light chain (VL) sequence of single-chain variable region derived from BCMA-1 antibody:

```
                                           (SEQ ID NO: 7)
DIVLTQSPPSLAMSLGKRATISCRASESVTILGSHLIHWYQQKPGQPPTL

LIQLASNVQTGVPARFSGS GSRTDFTLTIDPVEEDDVAVYYCLQSRTIP

RTFGGGTKLEIK
```

(3) heavy chain (VH) sequence of single-chain variable region derived from BCMA-1 antibody:

```
                                           (SEQ ID NO: 8)
QIQLVQSGPELKKPGETVKISCKASGYTFTDYSINWVKRAPGKGLKWMGW

INTETREPAYAYDFRGRFAFSLETSASTAYLQINNLKYEDTATYFCALDY

SYAMDYWGQGTSVTVSS
```

Among them, BCMA-1 is an antibody sequence contained in a published Car-T sequence, and is used as a control in the present application.

(4) light chain (VL) sequence of single-chain variable region derived from BCMA-20 antibody:

```
                                           (SEQ ID NO: 1)
DIQMTQSPSSLSASVGDRVTITCRASQGISNYLNWYQQKPGKAPKPLIYY

TSNLQSGVPSRFSGSGSGT DYTLTISSLQPEDFATYYCMGQTISSYTFG

QGTKLEI
```

(5) heavy chain (VH) sequence of single-chain variable region derived from BCMA-20 antibody:

```
                                           (SEQ ID NO: 2)
EVQLVESGGGLVQPGGSLRLSCAASGFTFSNFDMAWVRQAPGKGLVWVSS

ITTGADHAIYADSVKGRFTISRDNAKNTLYLQMNSLRAEDTAVYYCVRHG

YYDGYHLFDYWGQGTLVTVSS
```

(6) light chain (VL) sequence of single-chain variable region derived from BCMA-CA8 antibody:

```
                                           (SEQ ID NO: 3)
DIQLTQTTSSLSASLGDRVTISCSASTTTSNYLNWYQQKPDGTVELVIYY

TSNLHGGGPSRFSGSGSGTDYSLTIGYLEPEDVATYYCQQYRKLPWTFGG

GSKLEIKR
```

(7) heavy chain (VH) sequence of single-chain variable region derived from BCMA-CA8 antibody:

```
                                           (SEQ ID NO: 4)
EVQLQQSGAVLARPGASVKMSCKGSGYTFTNYWMHWVKQRPGQGLEWIGA

TYRGHSDTYYNQKFKGKAKLTAVTSTSTAYMELSSLTNEDSAVYYCTRGA

IYNGYDVLDNWGQGTLVTVSS
```

(8) light chain (VL) sequence of single-chain variable region derived from BCMA-MO6 antibody:

```
                                           (SEQ ID NO: 5)
DIQMTQSPSSLSASVGDRVTITCSASQDISNYLNWYQQKPGKAPKLLIYY

TSNLHSGVPSRFSGSGSGTDFTLTISSLQPEDFATYYCQQYRKLPWTFGQ

GTKLEIKR
```

(9) heavy chain (VH) sequence of single-chain variable region derived from BCMA-MO6 antibody:

```
                                           (SEQ ID NO: 6)
QVQLVQSGAEVKKPGSSVKVSCKASGGTFSNYWMHWVRQAPGQGLEWMGA

TYRGHSDTYYNQKFKGRVTITADKSTSTAYMELSSLRSEDTAVYYCARGA

IYDGYDVLDNWGQGTLVTVSS
```

(10) The linker sequence between heavy chain and light chain of BCMA-1 single-chain variable region is:

```
                                          (SEQ ID NO: 10)
              GSTSGSGKPGSGEGSTKG
```

(11) The linker sequence between heavy chain and light chain of BCMA-20, BCMA-CA8, and BCMA-M06 single-chain variable region is:

(SEQ ID NO: 11)
GGGGSGGGGSGGGGS

(12) Sequence of hinge region and linker region:

(SEQ ID NO: 12)
FVPVFLPAKPTTTPAPRPPTPAPTIASQPLSLRPEACRPAAGGAVHTRGL

DFACD

(13) The transmembrane region is a transmembrane region sequence of CD8 (CD8TM) antigen:

(SEQ ID NO: 13)
IYIWAPLAGTCGVLLLSLVITLYC

(14) The co-stimulatory factor signal region is derived from the sequence of 4-1BB cytoplasmic signaling motif:

(SEQ ID NO: 14)
KRGRKKLLYIFKQPFMRPVQTTQEEDGCSCRFPEEEEGGCEL

(15) The signaling region of CD3 zeta is derived from the sequence of immunoreceptor tyrosine-based activation motif (ITAM) of CD3zeta in the TCR complex:

(SEQ ID NO: 15)
RVKFSRSADAPAYQQGQNQLYNELNLGRREEYDVLDKRRGRDPEMGGKPQ

RRKNPQEGLYNELQKDKMAEAYSEIGMKGERRRGKGHDGLYQGLSTATKD

TYDALHMQALPPR

Chimeric Antigen Receptor T Cells (CAR-T Cells)

As used herein, the terms "CAR-T cell", "CAR-T", "CART", "CAR-T cell of the invention" all refer to the CAR-T cell of the second aspect of the invention.

The present invention relates to the construction of a chimeric antigen receptor structure targeting BCMA, a preparation method of a chimeric antigen receptor engineered T cell targeting BCMA, and activity identification thereof.

Vector

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The present invention also provides vectors in which the expression cassette of the present invention is inserted. Vectors derived from retroviruses such as the lentivirus are suitable tools to achieve long-term gene transfer since they allow long-term, stable integration of a transgene and its propagation in daughter cells. Lentiviral vectors have the advantage over vectors derived from onco-retroviruses such as murine leukemia viruses in that they can transduce non-proliferating cells, such as hepatocytes. They also have the advantage of low immunogenicity.

In brief summary, the expression cassette or nucleic acid sequence of the invention is typically and operably linked to a promoter, and incorporated into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immune and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al, (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionein promoter, a glucocorticoid promoter, a progesterone promoter, and a tetracycline promoter.

In order to assess the expression of a CAR polypeptide or portions thereof, the expression vector to be introduced into a ceil can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, and the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

In a preferred embodiment of the invention, the vector is a lentiviral vector.

Preparation

The invention provides a preparation comprising the CAR-T cell according to the first aspect of the invention, and a pharmaceutically acceptable carrier, diluent or excipient. In one embodiment, the preparation is a liquid preparation. Preferably, the preparation is an injection. Preferably, the concentration of the CAR-T cells in the preparation is $1\times10^3$–$1\times10^8$ cells/ml, more preferably $1\times10^4$–$1\times10^7$ cells/ml.

In one embodiment, the preparation may comprises buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. The preparation of the invention is preferably formulated for intravenous administration.

Therapeutic Application

The invention comprises therapeutic applications using cells (e.g., T cells) transduced with a lentiviral vector (LV)

encoding the expression cassette of the invention. The transduced T cells can target the tumor cell marker BCMA, synergistically activate T cells, and cause T cell immune responses, thereby significantly increasing the killing efficiency against tumor cells.

Thus, the present invention also provides a method for stimulating a T cell-mediated immune response to a target cell population or tissue in a mammal comprising the step of administering to the mammal a CAR-T cell of the invention.

In one embodiment, the present invention comprises a class of cell therapies, wherein T cells from autologous patient (or heterologous donor) are isolated, activated and genetically modified to generate CAR-T cells, and then injected into the same patient. The probability of graft versus host disease in the way is extremely low, and antigens are recognized by T cells in a non-MHC-restricted manner. In addition, one CAR-T can treat all cancers that express the antigen. Unlike antibody therapies, CAR-T cells are able to replicate in vivo resulting in long-term persistence that can lead to sustained tumor control In one embodiment, the CAR-T cells of the invention can undergo robust in vivo T cell expansion and can persist for an extended amount of time. In addition, the CAR mediated immune response may be part of an adoptive immunotherapy approach in which CAR-modified T cells induce an immune response specific to the antigen binding moiety in the CAR. For example, an anti-BCMA CAR-T cell elicits an immune response specific against cells expressing BCMA.

Although the data disclosed herein specifically disclose lentiviral vector comprising BCMA scFv, hinge and transmembrane domain, and 4-1BB and CD3ζ signaling domains, the invention should be construed to include any number of variations for each of the components of the construct as described elsewhere herein.

Cancers that may be treated include tumors that are unvascularized or largely unvascularized, and tumors that are vascularized. Cancers may include non-solid tumors (such as hematological tumors, for example, leukemias and lymphomas) or solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyeiocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, mesothelioma, malignant lymphoma, pancreatic cancer and ovarian cancer.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expanding the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

In addition to using a cell-based vaccine in terms of ex vivo immunization, the present invention also provides compositions and methods for in vivo immunization to elicit an immune response directed against an antigen in a patient.

The present invention provides methods for treating tumors comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2, IL-17 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

The administration of the subject compositions may be carried out in any convenient manner, including by aerosol inhalation, injection, ingestion, transfusion, implantation or transplantation. The compositions described herein may be administered to a patient subcutaneously, intradermaliy, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunotherapeutic agents. In a further embodiment, the cell compositions of the present invention are administered to a patient in conjunction with (e.g., before, simultaneously or following) bone marrow transplantation, or the use of chemotherapy agents such as, fludarabine, external-beam radiation therapy (XRT), cyclophosphamide. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for patient administration can be performed according to art-accepted practices. In general, $1 \times 10^6$ to $1 \times 10^{10}$ of the modified T cells of the invention (e.g., CAR-T-BCMA cells) can be applied to patients by means of, for example, intravenous infusion each treatment or each course of treatment.

The main advantages of the present invention are:

(a) As for the chimeric antigen receptor of the present invention, the extracellular antigen binding domain is a specific anti-BCMA scFv; the CAR formed by binding the specific anti-BCMA scFv to a specific hinge region and an intracellular domain shows a great ability of killing tumor cells with low cytotoxicity and low side effects.

(b) The chimeric antigen receptor provided by the invention can achieve stable expression and membrane localization of CAR protein after T cells infected by lentivirus carrying CAR gene.

(c) The CAR-modified T cells of the present invention have a longer survival time in vivo and strong anti-tumor effect. The scFv used in the present invention is a humanized or human-derived antibody, and is less likely to produce specific immunological rejection.

The present invention will be further illustrated below with reference to the specific examples. It is to be understood that these examples are for illustrative purposes only and are not intended to limit the scope of the invention. For the experimental methods in the following examples the specific conditions of which are not specifically indicated, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified. Percentages and parts are by weight unless otherwise stated.

Example 1

Construction of Lentiviral Expression Vector

The full-length DNA synthesis and cloning were commissioned by Shanghai Boyi Biotechnology Co., Ltd to achieve the construction of coding plasmids. The pWPT lentiviral vector was selected as a cloning vector, and the cloning sites were BamHI and SalI sites. The specific sequence is as described above.

Example 2

Preparation of CAR-T Cell (1) Mononuclear cells (PBMCs) were isolated from venous blood of healthy people by density gradient centrifugation.

(2) On day 0, PBMCs were seeded in a cell culture flask previously coated with CD3 monoclonal antibody (OKT3) at a final concentration of 5 μg/mL and Retronectin (purchased from TAKARA) at a final concentration of 10 μg/mL. The medium was GT-551 cell culture medium containing 1% human albumin. Recombinant human interleukin 2 (IL-2) was added to the medium at a final concentration of 1000 U/mL. The cells were cultured in an $CO_2$ incubator with a saturated humidity of 5% at 37° C.

(3) On day 1, the supernatant of the cultured PBMCs was slowly aspirated and discarded. New GT-551 cell culture medium containing 1% human albumin was added, and recombinant human interleukin 2 (IL-2) was added to the medium at a final concentration of 1000 U/mL. The cells were continuously cultured in an $CO_2$ incubator with a saturated humidity of 5% at 37° C.

(4) On day 3, fresh medium, concentrated and purified CAR-BCMAs lentivirus solution, protamine sulfate (12 ug/ml), and IL-2 (at a final concentration of 1000 U/mL) were added. After 12 hours of infection in a 5% $CO_2$ incubator at 37° C., the culture medium was discarded, fresh medium was added, and cultivation was continued in a 5% $CO_2$ incubator at 37° C.

(5) Starting from day 6, CAR-BCMAs cells can be taken for the corresponding activity assay.

Example 3

Detection of the Integration Rate of the CAR Gene in the T Cell Genome and the Expression Level of the Encoded Protein Thereof on the Membrane Surface $0.5 \times 10^6$ of CART-BCMAs cell samples cultured on day 7 (FIG. 3A), day 21 (FIG. 3B) and day 29 (FIG. 3C) in Example 2 were taken, respectively. The expression level of CAR-BCMA protein on the surface of T cell membrane was analyzed by flow cytometry after Fc fragment staining of recombinant human BCMA protein.

The result is shown in FIGS. 3A, 3B, and 3C, and four CAR structures designed in the present invention can be expressed in their corresponding modified T cells and complete the cell membrane surface localization.

Example 4

Detection of the In Vitro Activation Ability of CAR-BCMAs

Cell activation level indicator proteins CD137 and IFNγ was detected using CART-BCMAs cells cultured on day 7 in Example 2. $1\times10^5$ of CART-BCMA cells cultured on day 7 were cultured respectively with BCMA-positive K562-BCMA+E7 tumor cell line and BCMA-negative K562 tumor cell line, or without tumor cells, in 200 μl GT-551 medium for 18 h at a ratio of 1:1. Then the expression level of CD137 on the surface of T cell membrane was detected by flow cytometry and the secretion level of IFNγ in the culture supernatant was detected by ELISA.

Figure 4A:
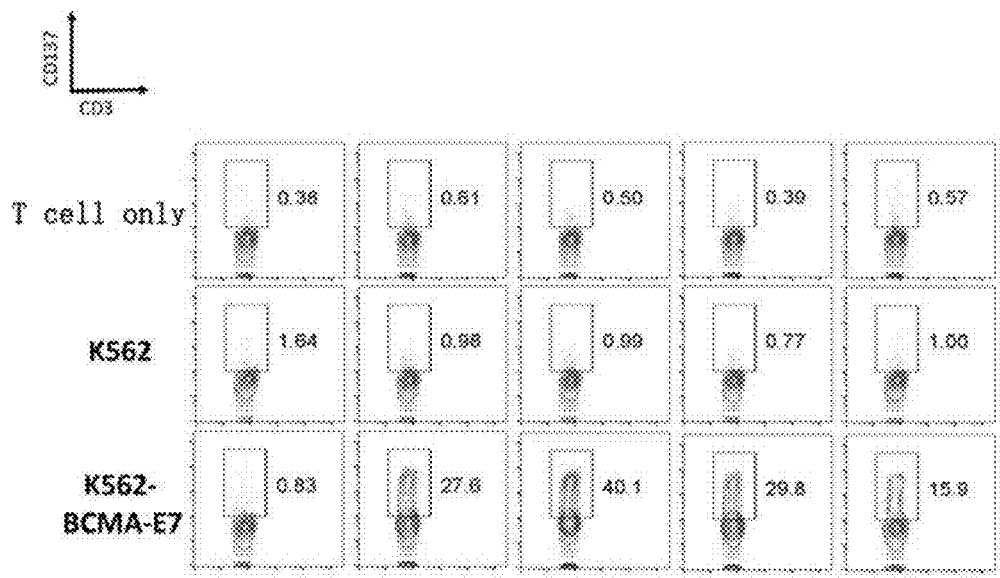
FIGS. 4A and 4B show the expression level of CD137 on the surface of T cell membrane (FIG. 4A) and the secretion level of IFNγ in the culture supernatant (FIG. 4B). Specifically, 1×$10^5$ of CART-BCMA cells cultured on day 7 were cultured respectively with BCMA-positive K562-BCMA-E7 tumor cell line and BCMA-negative K562 tumor cell line, or without tumor cells, in 200 µl GT-551 medium for 18 h at a ratio of 1:1. Then the expression level of CD137 on the surface of T cell membrane and the secretion level of IFNγ in the culture supernatant was detected respectively.
Figure 4B:
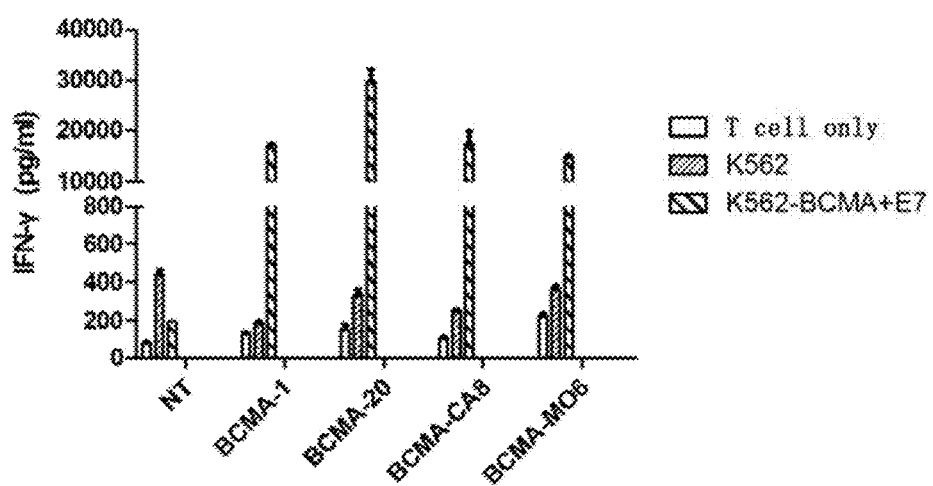

The results are shown in FIGS. 4A and 4B, the expression of CD137 was detected on the surface of four CART cells, and the expression of IFNγ was detected in the culture supernatant. Among them, CAR-BCMA-20 shows best CD137 activation level and IFNγ release level. CART-BCMA-MO6 which is constructed based on humanized MO6 antibody sequence shows a weaker level of CD137 activation but a higher level of IFNγ release than CART-BCMA-CA8 which is constructed based on mouse antibody sequence.

Example 5

Figure 5:
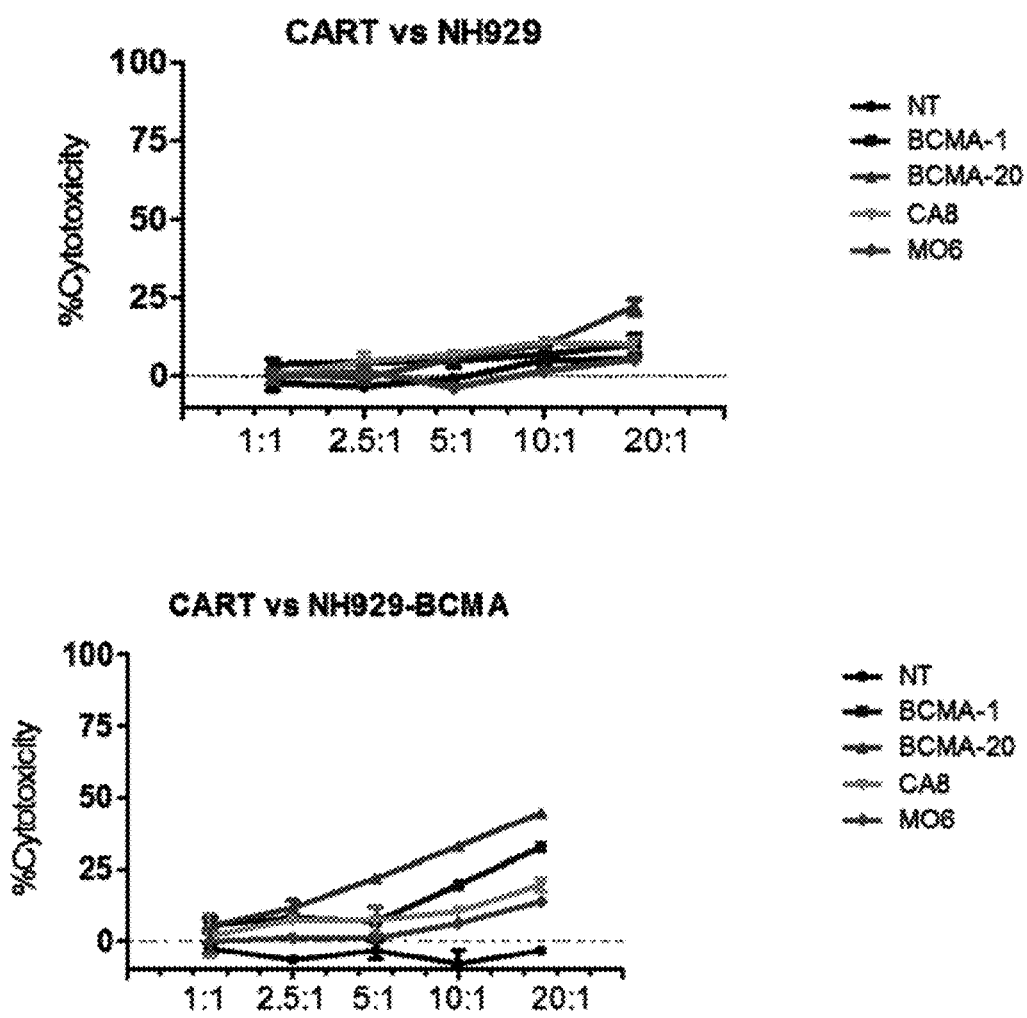
FIG. 5 shows detection of advanced apoptosis level of tumor cells induced by CART-BCMAs. Specifically, 1×$10^4$ CFSE-labeled BCMA-negative (NH929) or BCMA-positive (NH929-BCMA) tumor cell lines were co-cultured respectively with corresponding T cells in 100 µl of GT-551 medium for 4 h at a ratio as shown in the figure. The proportion of PI-positive cells in CFSE-positive cells was analyzed by flow cytometry after staining with 100 µl of 25% PI dye for 15 min. The figure shows the statistical analysis of PI positive cells in the corresponding co-culture samples.

Detection of Advanced Apoptosis Activity of Tumor Cells Induced by CART-BCMAs Cells (1) The CART-BCMAs cells cultured on day 17 in Example 2 were mixed respectively with $1\times10^4$ CFSE-labeled BCMA-negative cells (NH929) or BCMA-positive self-constructed cells (NH929-BCMA overexpressing tumor cell line) at a ratio of 1:1, 2.5:1, 5:1, 10:1, 20:1 (as shown in FIG. 5). The mixed cells were co-cultured in 100 μl GT-551 medium for 4 h, and then stained with 100 μl 25% PI dye for 15 min. The proportion of PI positive cells in CFSE positive cells was analyzed by flow cytometry.

Figure 6A:
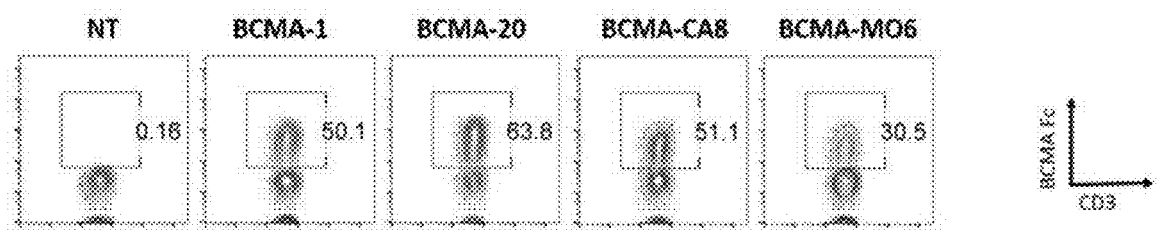
FIGS. 6A and 6B show detection of advanced apoptosis level of tumor cells induced by CART-BCMAs.
Figure 6B:
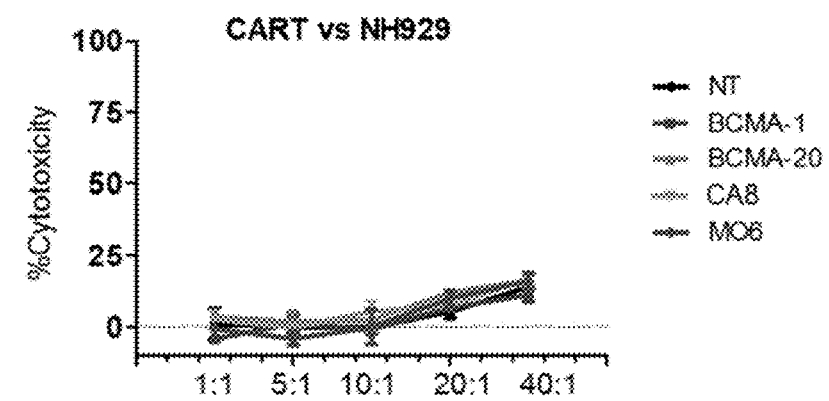
Figure 6B:
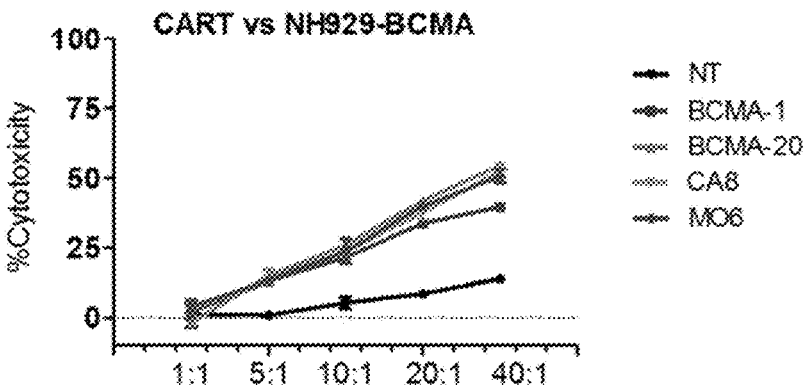
Figure 6B:
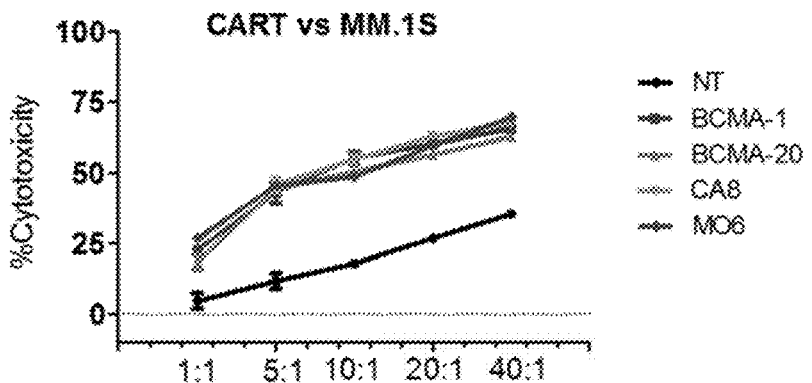

(2) The CART-BCMAs cells cultured on day 22 in Example 2 were mixed respectively with $1\times10^4$ CFSE-labeled BCMA-negative cells (NH929), BCMA-positive self-constructed cells (NH929-BCMA overexpressing tumor cell line) or MM.1S cell line naturally expressed BCMA at a ratio of 1:1, 5:1, 10:1, 10:1, 40:1 (as shown in FIG. 6B). The mixed cells were co-cultured in 100 μl GT-551 medium for 4 h, and then stained with 100 μl 25% PI dye for 15 min. The proportion of PI positive cells in CFSE positive cells was analyzed by flow cytometry.

The results are shown in FIGS. 5, 6A, and 6B, all four CART cells can induce apoptosis of BCMA-positive tumor cells. Among them, CART-BCMA-20 can induce advanced apoptosis of BCMA-positive tumor cells better than CART-BCMA-1. The ability of CART-BCMA-MO6 and CART-BCMA-CA8 to induce advanced apoptosis of BCMA-positive tumor cells is similar.

Example 6

Inhibition of CART-BCMAs on RPMI-8226 Myeloma Xenograft Model

RPMI-8226 cells in logarithmic growth phase were collected, and $4.0\times10^6$ tumor cells were inoculated subcutaneously in the right back of 6-8 week old B-NDG mice. When the tumor volume reached about 120 mm³, the animals were randomly divided into 4 groups according to tumor volume, so that the tumor volume difference of each group was less than 10% of the mean value. Then the solvent control, $7.5\times10^6$ NT and $7.5\times10^6$ CART-BCMAs cells were injected through tail vein respectively.

Figure 7A:
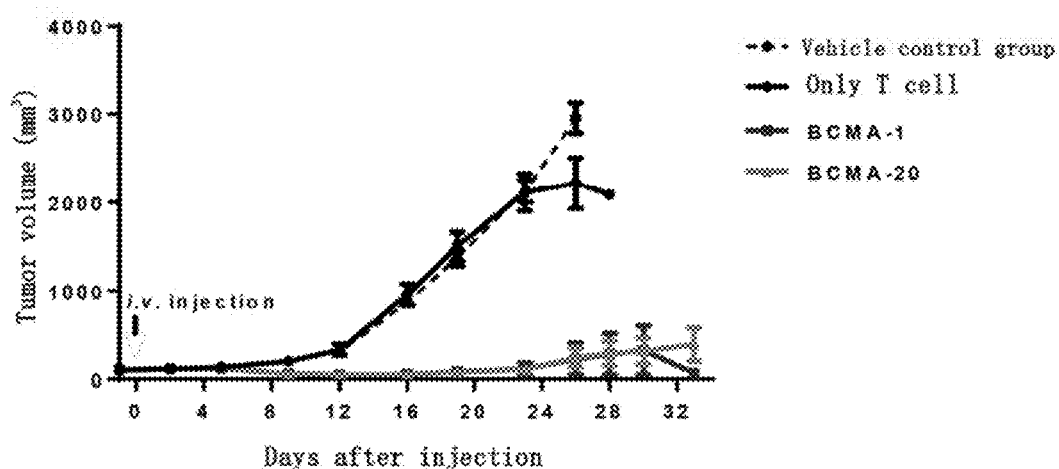
FIGS. 7A and 7B show the inhibitory effect of CART-BCMAs on the proliferation in vivo of myeloma cell line RPMI-8226 in B-NDG mice. RPMI-8226 cells in logarithmic growth phase were collected, and 4.0×$10^6$ tumor cells were inoculated subcutaneously in the right back of mice. When the tumor volume reached about 120 mm$^3$, the animals were randomly divided into 4 groups according to tumor volume. Then solvent control, 7.5×$10^6$ NT (T cells only) and 7.5×$10^6$ CART-BCMAs cells were injected through tail vein respectively.
Figure 7B:
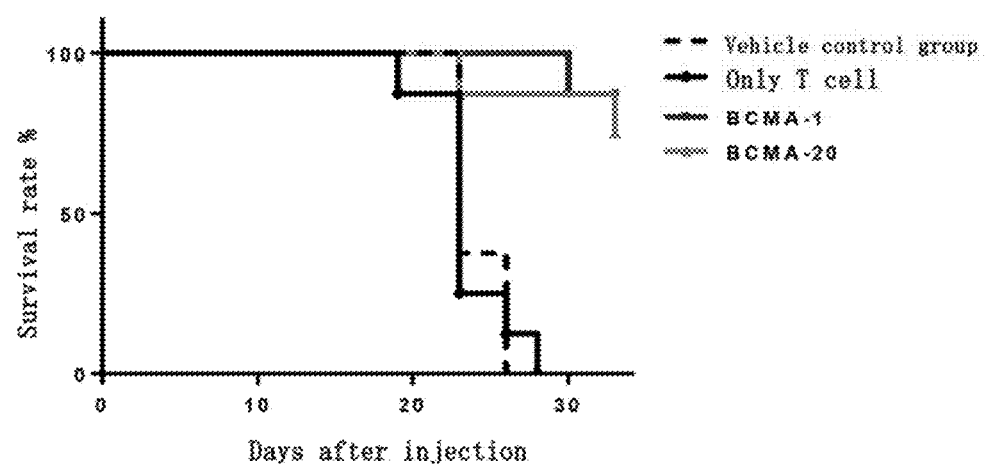

The results are shown in FIGS. 7A and 7B, compared with the control group, single injection of CART-BCMA-1 and CART-BCMA-20 through tail vein can effectively inhibit the growth of human myeloma RPMI-8226 cells (relative tumor proliferation rate % T/CRTV≤40%, P<0.05), and can significantly prolong the survival time of human myeloma-bearing mice (median survival of the control group is 23 days, median survival of the CART-BCMAs treatment group>33 days). There was no significant difference in tumor proliferation rate and median survival between the mice treated with CART-BCMA-1 and CART-BCMA-20.

Comparative Example

In the screening process of the chimeric antigen receptor of the present application, the inventors tested a large number of candidate sequences, which are illustrated below with examples.

The antibodies to be screened include: BCMA-1, BCMA-2, BCMA-69, BCMA-72, BCMA-2A1, BCMA-1E1, BCMA-J22.9, BCMA-20, BCMA-CA8, and BCMA-MO6. Structures of chimeric antigen receptor targeting BCMA were constructed on the basis of the above antibodies. Among them, BCMA-1 and BCMA-2 are published Car-T sequences and used as a positive control for screening. CAR-T cells were prepared in the same way as in Example 2, and detected in the same way as in Examples 3 and 4.

Figure 1B:
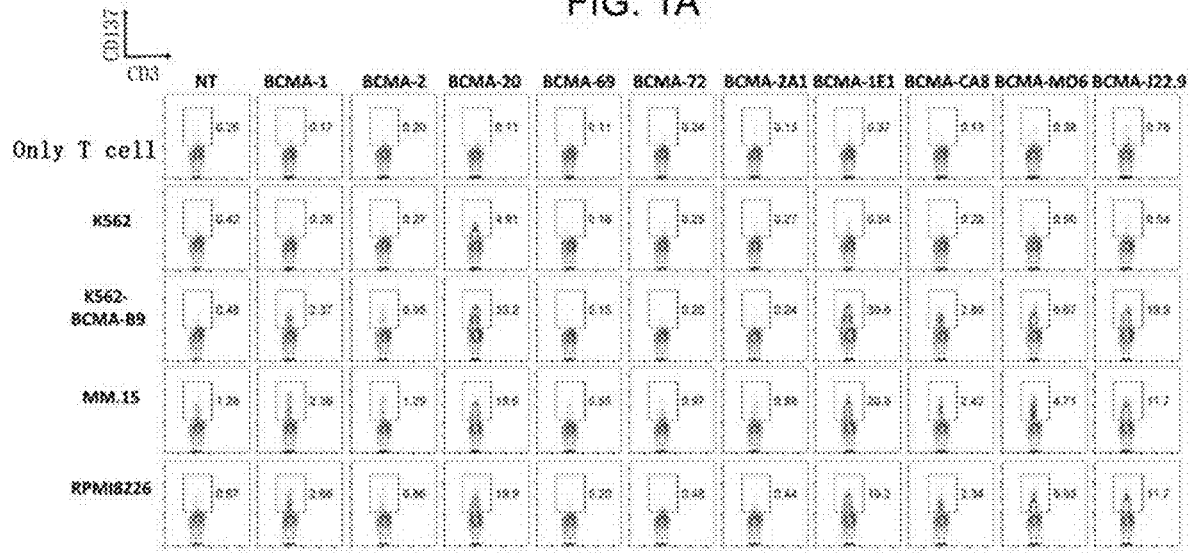
Figure 1C:
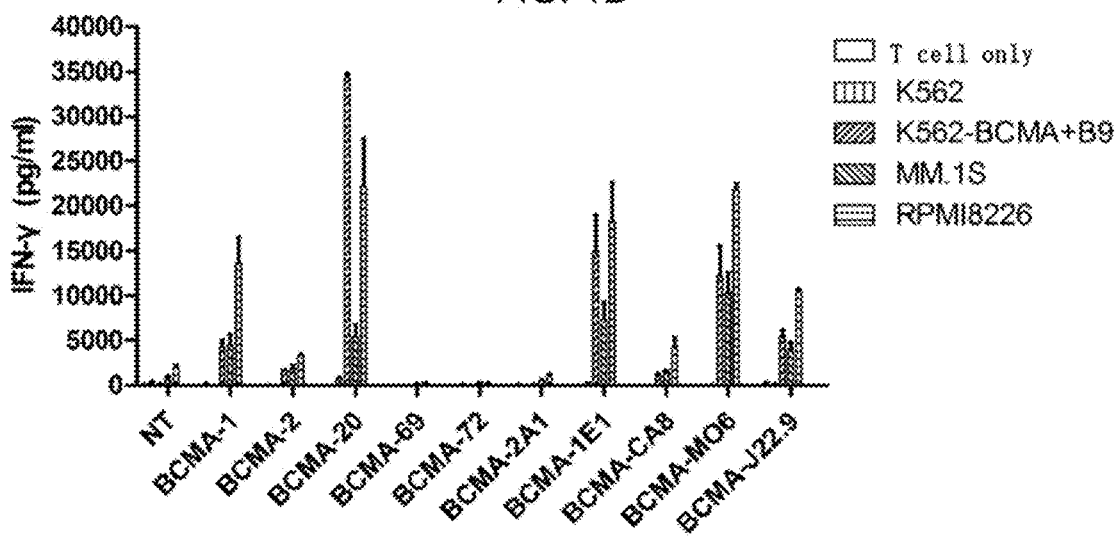

The results are shown in FIGS. 1A, 1B, and 1C, which are the experimental results of two batches of CAR-T cells. The expression of Car-T was detected with BCMA-Fc fusion protein. It can be seen that there is a high expression in primary T cells, as seen in FIG. 1A. In FIG. 1B, it can be seen that BCMA-1, BCMA-20, BCMA-1E1, BCMA-CA8, BCMA-MO6, and BCMA-J22.9 can be activated by the BCMA antigen. FIG. 1C shows that the activated BCMA-1, BCMA-20, BCMA-1E1, BCMA-CA8, BCMA-MO6, and BCMA-J22.9 CAR-Ts can produce higher levels of IFN-γ. The results show that the CAR-T functions obtained by BCMA-1, BCMA-20, CA8 and MO6 are similar, so BCMA-20, CA8 and MO6CAR-T were further analyzed and studied.

Example 7 Membrane Protein Array Experiment

The light chain variable region of SEQ ID NO: 1 and the heavy chain variable region of SEQ ID NO: 2 were used to prepare a single chain antibody B20-scFv-rabFc, and membrane protein array experiment was performed.

20 ug/mL of B20-scFv-rabFc was added to HEK293T cell array transiently transfected with 5344 membrane proteins, respectively. Flow cytometry found that, under this test condition, B20-scFv-rabFc may cross-recognize with TNFRSF17 (Q02223), MAG (P20916), CR2 (P20023), CXADR (P78310) and DDR2 (Q16832), wherein TNFRSF17, i.e. BCMA is the specific target of B20-scFv, and MAG, CR2, CXADR and DDR2 are suspected non-specific targets.

To further confirm whether the suspected target can cause the activation of CAR-T, CBM.BCMA CAR-T was co-cultured with 293T cells transfected with BCMA, CR2, CXADR, DDR2, and MAG, respectively. The IFNγ, TNF, IL-2 and other cytokines in co-culture supernatant were detected. 293T cells transfected with empty vector were used as a negative control, and 293T cells transfected with BCMA were used as a positive control.

Figure 8:
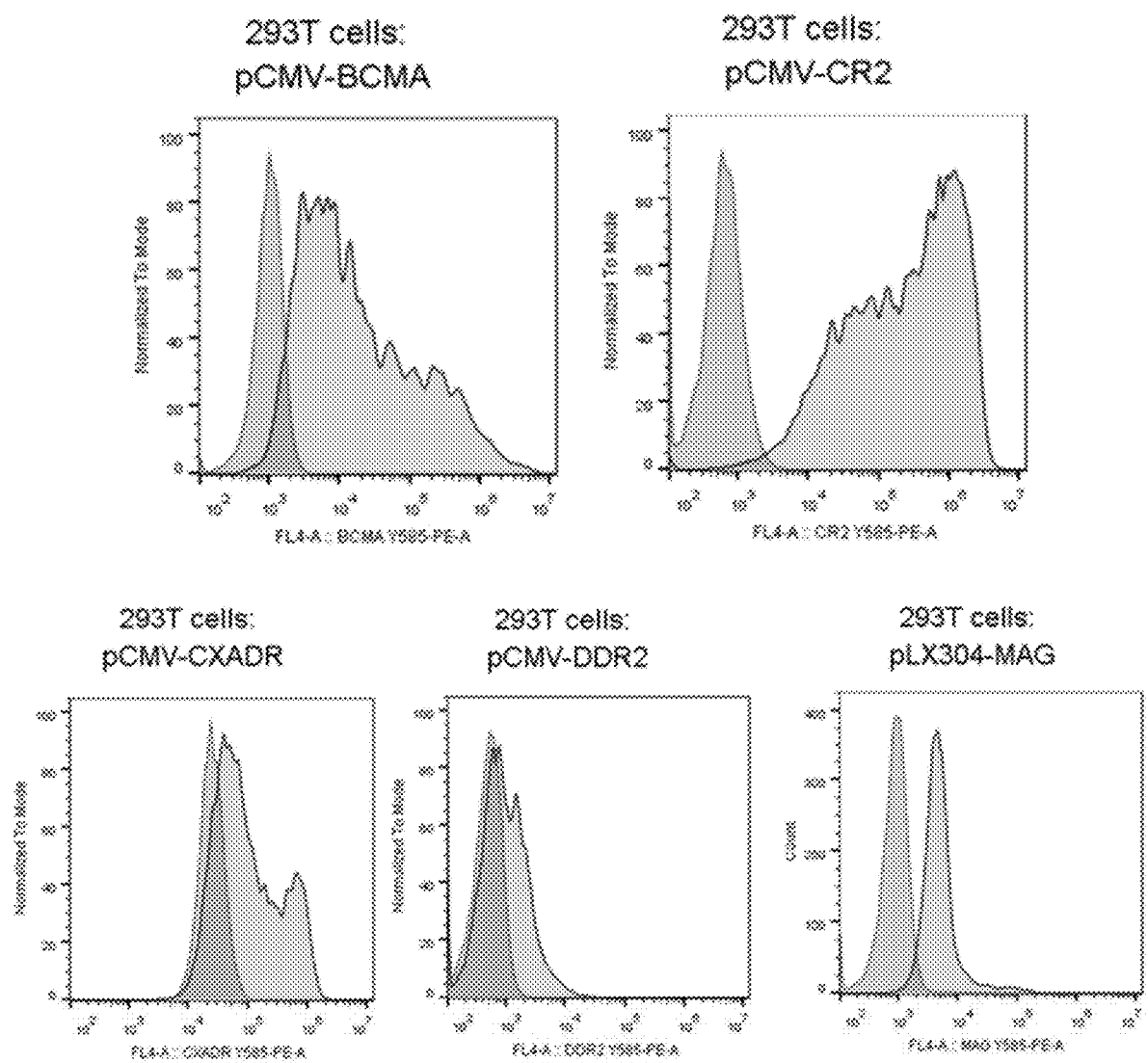
FIG. 8 shows results the expression of BCMA, CR2, CXADR, DDR2, and MAG in 293T cells after transfection of relevant plasmids by flow cytometry

FIG. 8 shows results the expression of BCMA, CR2, CXADR, DDR2, and MAG in 293T cells after transfection of relevant plasmids by flow cytometry.

Figure 9A:
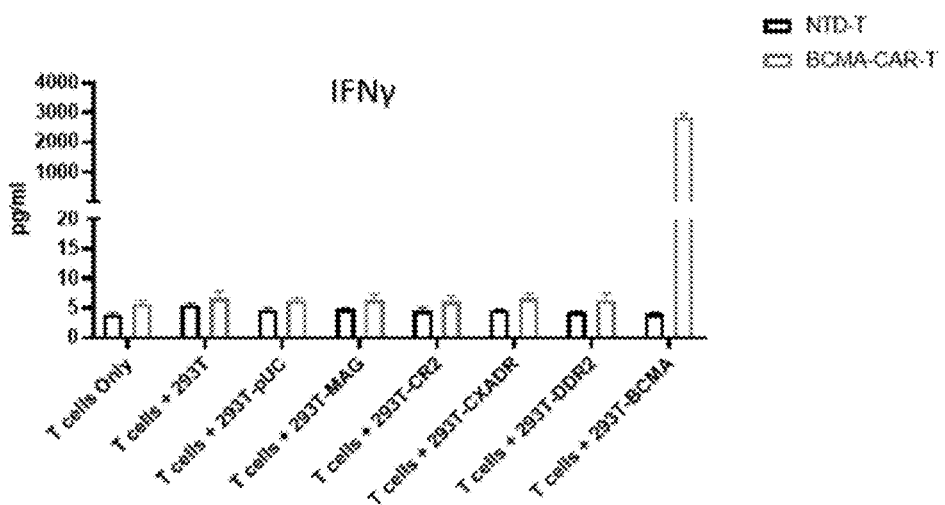
FIGS. 9A, 9B, and 9C show the cytokine detection results.
Figure 9B:
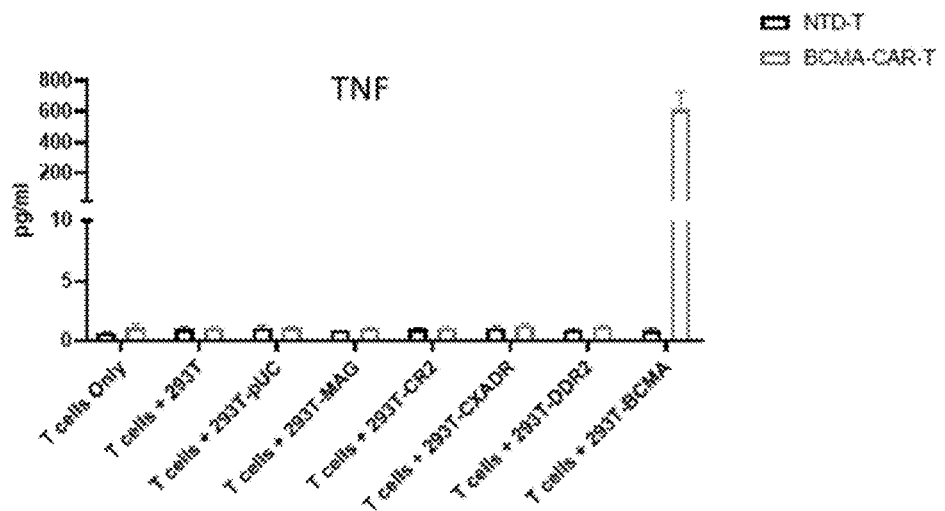
Figure 9C:
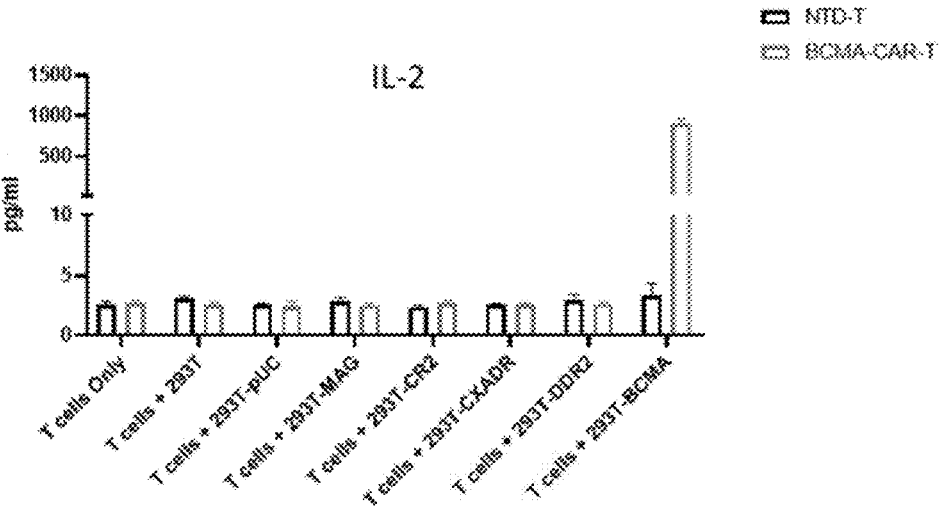

The cytokine detection results are shown in FIGS. 9A, 9B, and 9C. Only the BCMA expressed on 293T cells can induce CBM. BCMA CAR-T cells to produce large amounts of IFNγ/TNF/IL-2, while the other four non-specific surface markers cannot activate CBM. BCMA CAR-T cells.

Example 8 In Vitro Anti-Tumor Activity of C-CAR088 Cells

The chimeric antigen receptor BCMA-20 (hereafter named C-CAR088) was selected for subsequent experiments. C-CAR088 cells, NT cells (non-transfected T cells, used as negative control) and positive control cells (Bluebird bb2121) were co-cultured with BCMA negative cells (NH929) or BCMA positive cells (NH929-BCMA) at different effect target ratios, The killing ability of each cell to the target cell was analyzed.

Figure 10:
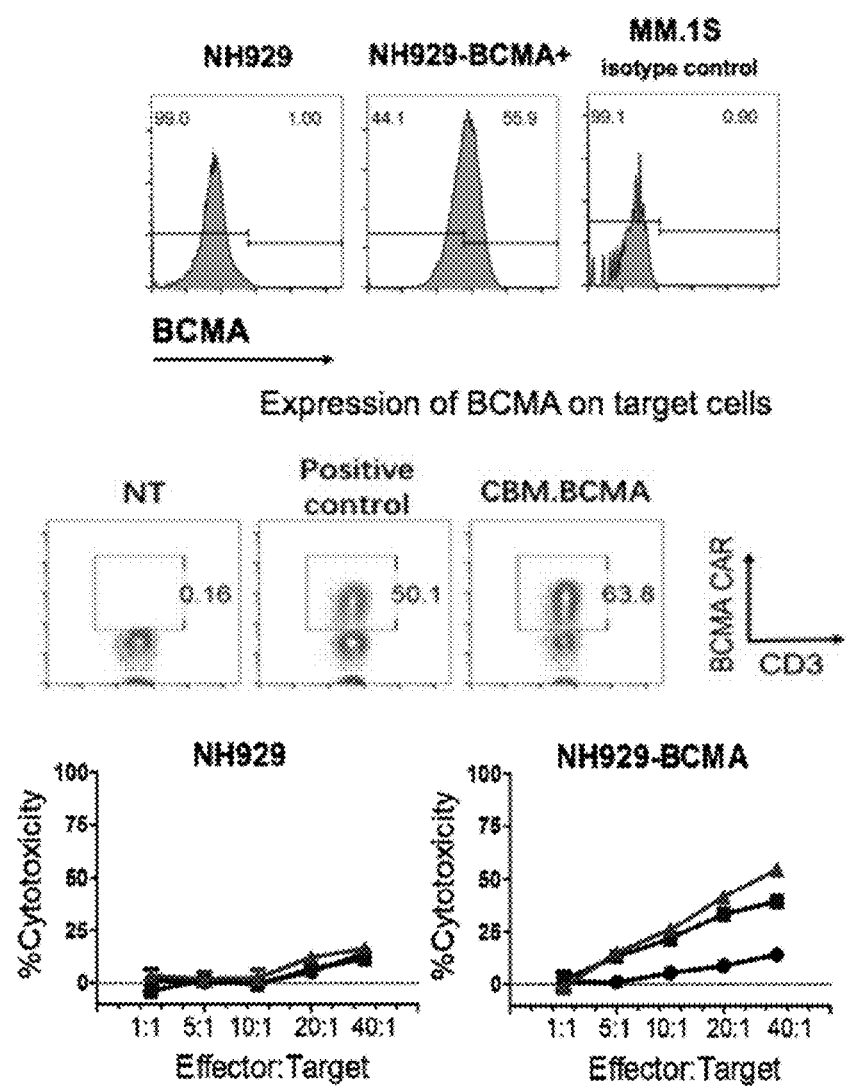
FIG. 10 shows the killing ability of each cell to the target cell.

The results are shown in FIG. 10. C-CAR088 cells and positive control cells only have a strong killing effect on NH929-BCMA cells, but no significant killing effect on negative target cells NH929. The non-transfected group (NT) also have no significant killing effect on the target cells.

Example 9 Effect of Soluble BCMA on Cell Killing Activity

In the co-cultivation system of C-CAR088 cells with BCMA negative target cells A549 and BCMA positive target cells A549-BCMA-2E9, 100 ng/ml and 500 ng/ml soluble BCMA protein was added respectively to detect its effect on CD137 expression.

Figure 11:
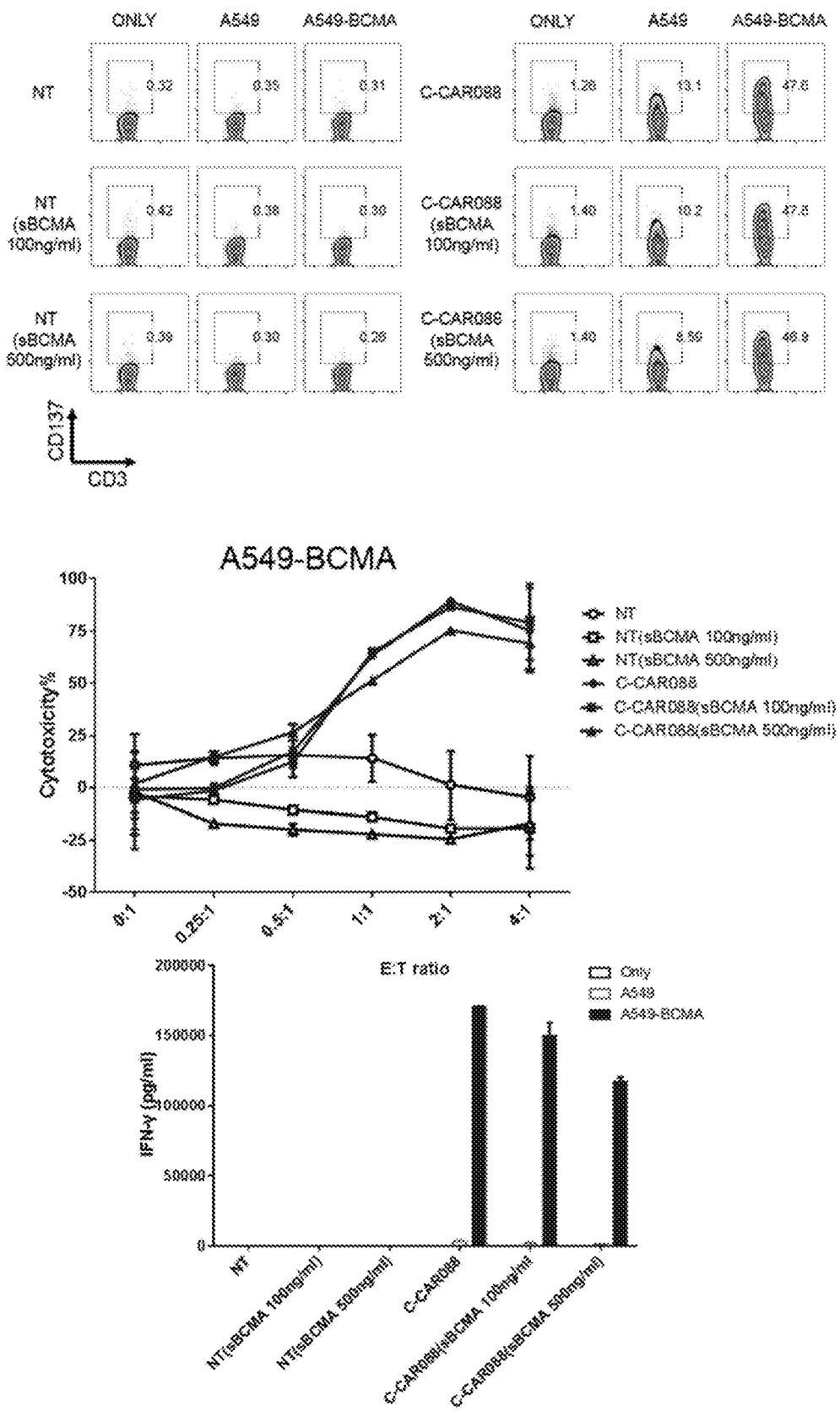
FIG. 11 shows the effect of soluble BCMA on cell killing activity.

The results are shown in FIG. 11. Soluble BCMA protein have no effect on the upregulation of CD137 expression, indicating that soluble BCMA does not block the specific recognition of CAR and target antigen. In the test of in vitro cell killing ability and ELISA of IFN-γ release, the killing effect of C-CAR088 cells on target cells and the release of IFN-γ were reduced by 500 ng/ml soluble BCMA protein, but there was no significant difference. The above results indicate that the cell killing activity of C-CAR088 cells is basically unaffected by soluble BCMA Example 10 Dose Dependent Effect of C-CAR088 Cells 6 week old B-NDG mice (half male and half female) were selected and intraperitoneally injected with $2.5 \times 10^6$ human multiple myeloma cells RPMI-8226. Mice with similar tumor burden were selected and divided into 5 groups, and were injected with $2.5 \times 10^6$ C-CAR088 cells (low-dose group), $5 \times 10^6$ C-CAR088 cells (medium-dose group), $1 \times 10^7$ C-CAR088 cells (high-dose group), T cells and vehicle (with cryoprotectant (CBMG C-CFMC) as vehicle), respectively. The experiment lasted 54 days. During the experiment, the tumor burden of the mice was evaluated every 5 days. At the end of the experiment, the survival rate of the mice was calculated.

Figure 12:
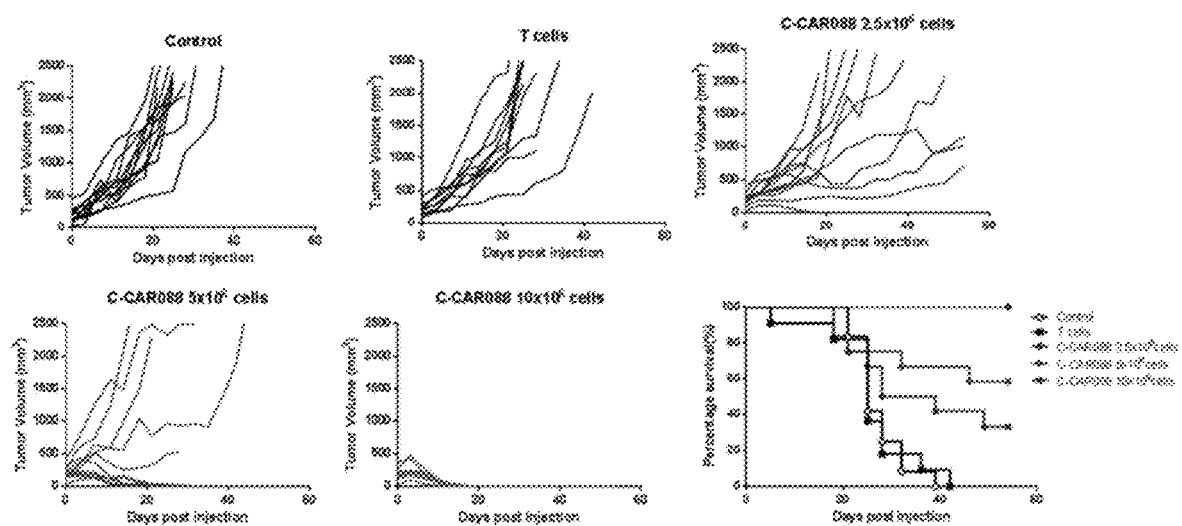
FIG. 12 shows the survival rate of the mice in each group.

The results are shown in FIG. 12. Single administration of doses of $5 \times 10^6$ cells/mouse and $1 \times 10^7$ cells/mouse C-CAR088 cells can effectively inhibit the growth of B-NDG mouse xenograft tumor of human myeloma RPMI-8226 cell. The relative tumor proliferation rates were 6.12% and 0.75%, respectively ($p<0.05$). At the end of the experiment, the survival rate of tumor-bearing mice in the middle-dose group was 91.7% (11/12). No death occurred in the tumor-bearing mice in the high-dose group, and the survival rate was 100.0% (12/12), having a significant difference ($p<0.05$) compared with the vehicle group (survival rate 58.3%). The above results indicate that C-CAR088 exhibits dose dependent in vivo anti-tumor activity.

Example 11 Phase I Clinical Study of C-CAR088

With the approval of the Ethics Committee, a total of 15 volunteers conducted phase I clinical trials. The key eligibility criteria for volunteer are as follows: patients with multiple myeloma aged 18-75 years old, MM cells express BCMA, have measurable MM, and have received 2 prior lines of therapy for MM and have received treatment with PI and IMiD, have adequate hepatic, renal, cardiac and hematopoietic function.

Figure 13:
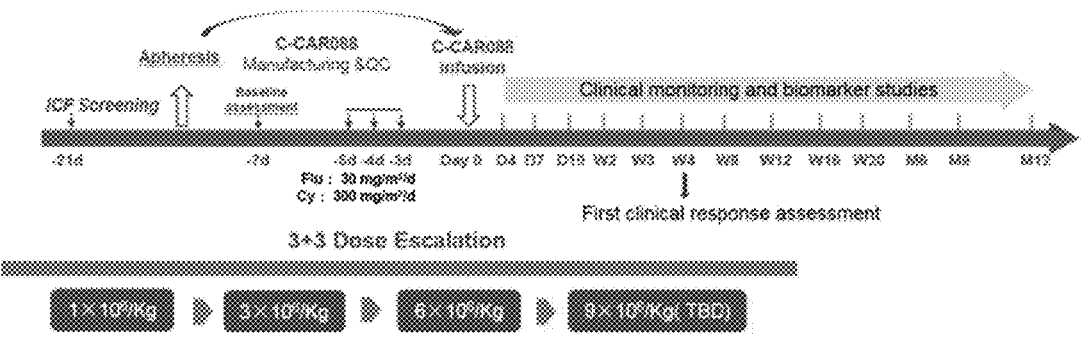
FIG. 13 shows the experimental process of phase I clinical study.

The experimental process is shown in FIG. 13.

Figure 14:
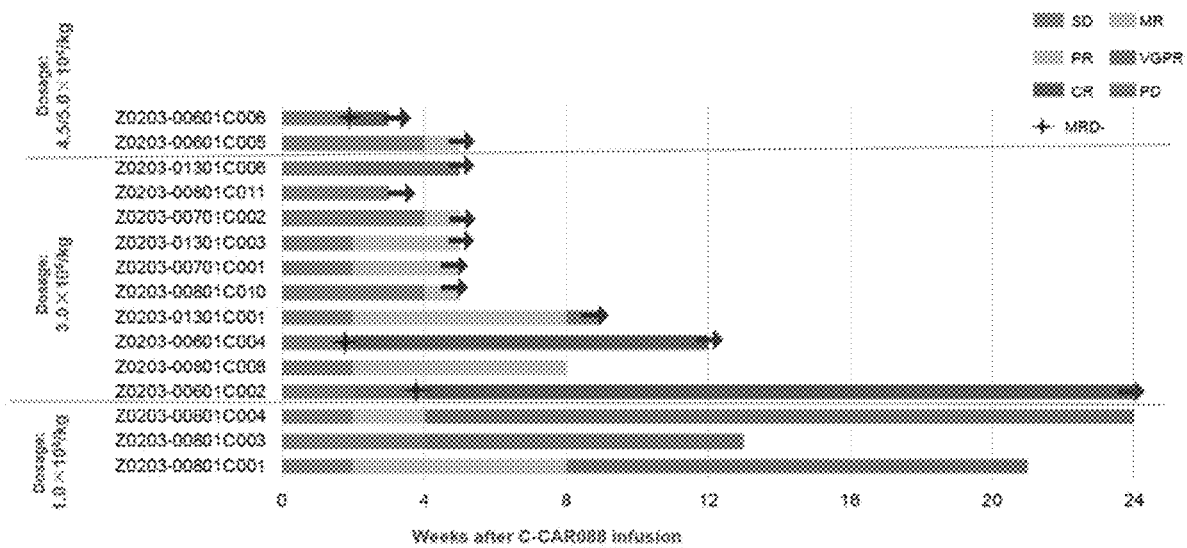
FIG. 14 shows the clinical response of phase I clinical study.

The treatment results are shown in FIG. 14 and Table 12. Two patients were evaluated at week 2, one SD and one CR. The remaining 13 patients were evaluated at week 4 and the objective response rate ORR reached 100%. In all patients, there were 3 CR, 5 VGPR (including 1 Daratumumab-resistant patient), and 6 PR.

TABLE 12

| | | | | Clinical response | | |
|---|---|---|---|---|---|---|
| Research center | Patient ID | Follow up length | Serum M protien /sFLC type | Baseline | 2 w | 4 w |
| | | | | | Clinical response | |
| Jiangsu Provincial People's Hospital | Z0203-00801C001 | 6 m | IgG | 71.0 g/L | 42.0 g/L | 26.3 g/L |
| | Z0203-00801C003 | 12 w | k | 3250 mg/L | 3050 mg/L | 75 mg/L SIF(−) UIF(+) UPEP(−) |

TABLE 12-continued

| Research center | Patient ID | | | Clinical response | | |
|---|---|---|---|---|---|---|
| | Z0203-00801C004 | 6 m | IgG | 46.5 g/L | 7.9 g/L | 9.0 g/L |
| | Z0203-00801C008 | 20 w | IgG | 26.1 g/L | 9.1 g/L | 4.8 g/L |
| | Z0203-00801C010 | 4 e | IgG | 55.7 g/L | 45.4 g/L | 23.3 g/L |
| | Z0203-00801C011 | 3 w | IgG | 22.5 g/L | 18.8 g/L | |
| Tianjin Hematology Hospital | Z0203-01301C001 | 8 w | IgA | 16.7 g/L | 7.4 g/L | 3.6 g/L |
| | Z0203-01301C003 | 4 w | IgG | 50.2 g/L | 27.1 g/L | 15.0 g/L |
| | Z0203-01301C006 | 4 w | λ | 760 mg/L | SPEP(−) UIF(−) SIF(+) | SPEP(−) UIF(−) SIF(+) |
| Peking Union Medical College Hospital | Z0203-00701C001 | 4 w | IgG | 17.4 g/L | 10.8 g/L | 5.3 g/L |
| | Z0203-00701C002 | 4 w | IgG | 21.7 g/L | 15.8 g/L | 7.9 g/L |
| Daupei Hospital | Z0203-00601C002 | 12 w | λ | 187 mg/L | SIF− UIF− MRD− | SIF− UIF− MRD− |
| | Z0203-00601C004 | 4 w | κ | 209 mg/L | SIF− UIF− MRD− | SIF− UIF− MRD− |
| | Z0203-00601C005 | 4 w | IgG | 28.27 g/L | 24.3 g/L | 8.6 g/L |
| | Z0203-00601C006 | 2 W | κ | 121 mg/L | SIF− UIF− MRD− | |

| Research center | Patient ID | Clinical response | | | | | Best ORR |
|---|---|---|---|---|---|---|---|
| | | 8 w | 12 w | 16 w | 20 w | 6 m | |
| Jiangsu Provincial People's Hospital | Z0203-00801C001 | 1.8 g/L UIF(−) | 6.2 g/L UIF(−) | 7.0 g/L UIF(−) | 16.4 g/L | 45 g/L | VGPR |
| | Z0203-00801C003 | 170 mg/L | 960 mg/L | PD | | | VGPR |
| | Z0203-00801C004 | SPEP(−) UIF(−) SIF(+) | SPEP(−) UIF(−) SIF(+) | SPEP(−) UIF(−) SIF(+) | SPEP(−) UIF(−) SIF(+) | 21.6 g/L | VGPR |
| | Z0203-00801C008 | 4.6 g/L | 9 g/L* | 10 g/L* | 17 g/L * | PD | PR |
| | Z0203-00801C010 | | | | | | PR |
| | Z0203-00801C011 | | | | | | SD |
| Tianjin Hematology Hospital | Z0203-01301C001 | SPEP(−) UIF(−) SIF(+) | | | | | VGPR |
| | Z0203-01301C003 | | | | | | PR |
| | Z0203-01301C006 | | | | | | VGPR |
| Peking Union Medical College Hospital | Z0203-00701C001 | | | | | | PR |
| | Z0203-00701C002 | | | | | | PR |
| Daupei Hospital | Z0203-00601C002 | SIF− UIF− MRD− | SIF− UIF− MRD− | SIF− UIF− MRD− | SIF− UIF− MRD− | | sCR |
| | Z0203-00601C004 | SIF− UIF− MRD− | SIF− UIF− MRD− | | | | sCR |
| | Z0203-00601C005 | | | | | | PR |
| | Z0203-00601C006 | | | | | | sCR |

The treatment-emerging adverse events are shown in Table 13. Only one patient occurred grade 3 cytokine release syndrome in 15 patients. No neurotoxicity events and no dose-limiting toxicity (DLTs) were observed in the dose escalation. The cytopenias is mostly related to Cy/Flu lymphodepletion. It should be noted that the occurrence of a certain degree of cytokine release syndrome after treatment also illustrates the effectiveness of CART treatment from the side. None of the 15 patients had particularly serious cytokines, and C-CAR088 has better safety.

TABLE 13

Treatment-Emerging Adverse Events

| Treatment-Emerging Adverse Events | n (%) Overall | n (%) Grade 3/4 |
|---|---|---|
| Cytokine release syndrome | 14 (93) | 1 (7) |
| Neutropenia | 15 (100) | 15 (100) |
| Thrombocytopenia | 13 (87) | 11 (73) |
| Anemia | 12 (80) | 6 (40) |
| Increased AST | 5 (33) | 3 (20) |
| Infection | 3 (20) | 3 (20) |

Figure 15:
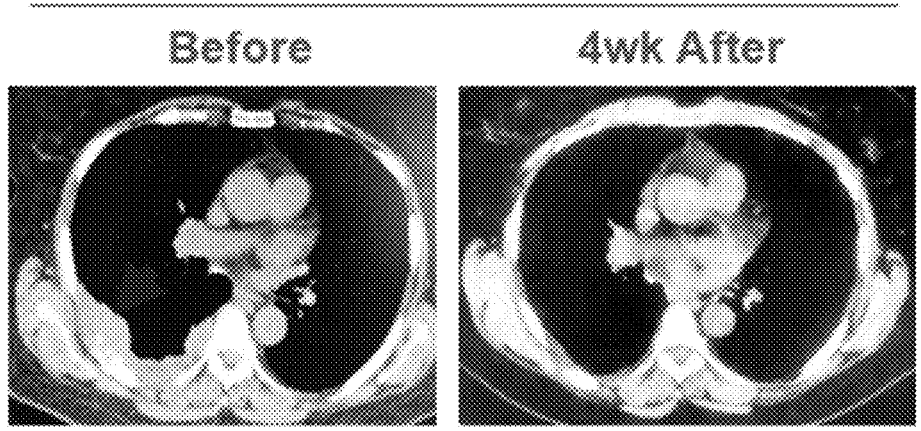
FIG. 15 shows the treatment condition of the patient of ID Z0203-00801C008.
Figure 15:
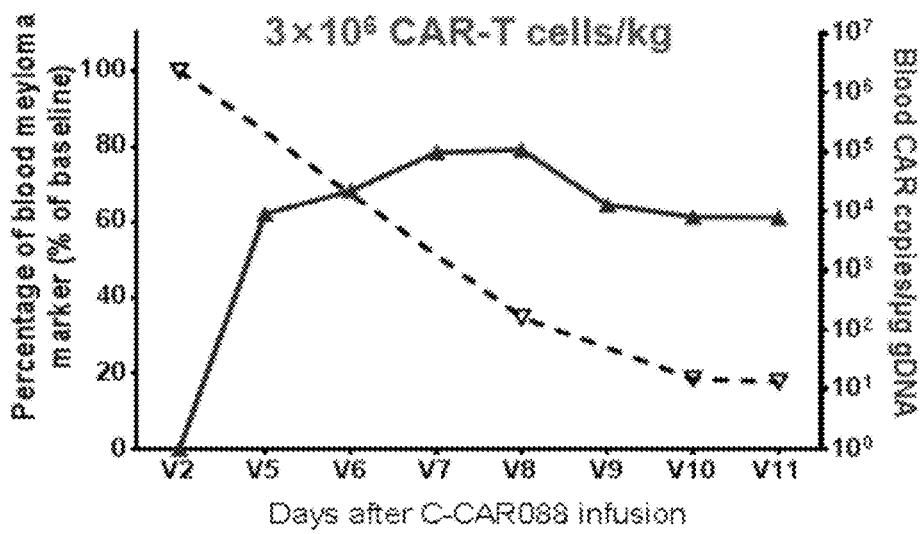
Figure 16A:
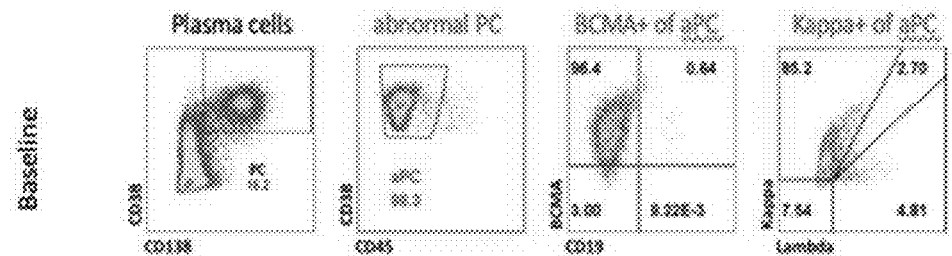
FIGS. 16A and 16B show the treatment condition of patient of ID Z0203-00701C001.
Figure 16B:
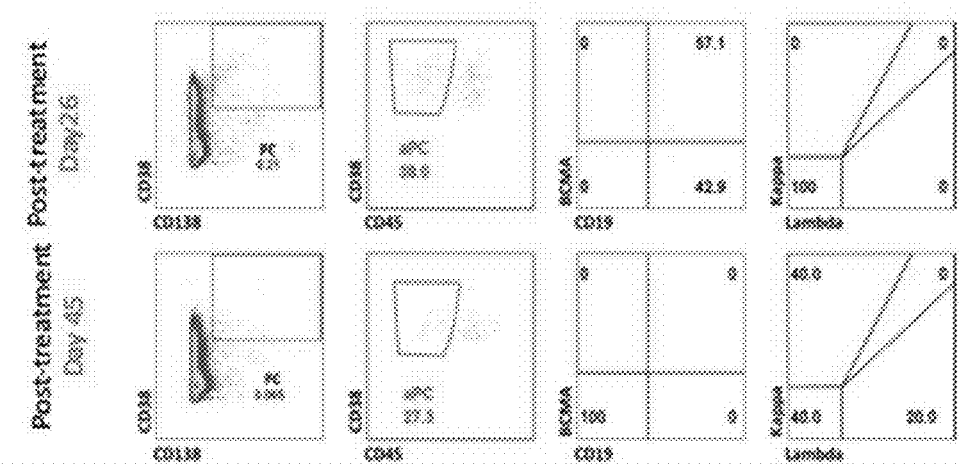

FIG. 15 shows the treatment condition of the patient of ID Z0203-00801C008. FIGS. 16A and 16B show the treatment condition of patient of ID Z0203-00701C001. FIG. 16A shows that majority of the PCs were abnormal (>90% were CD45lo/−), were BCMA+ and clonal for Kappa light chain at the beginning of the experiment (Baseline). FIG. 16B shows that after 14 or 28 days of BCMA CAR-T treatment, abnormal PC in BM were significantly decreased, especially Kappa+PC, which decreased from the baseline level of 85.2% to 0%.

Figure 17:
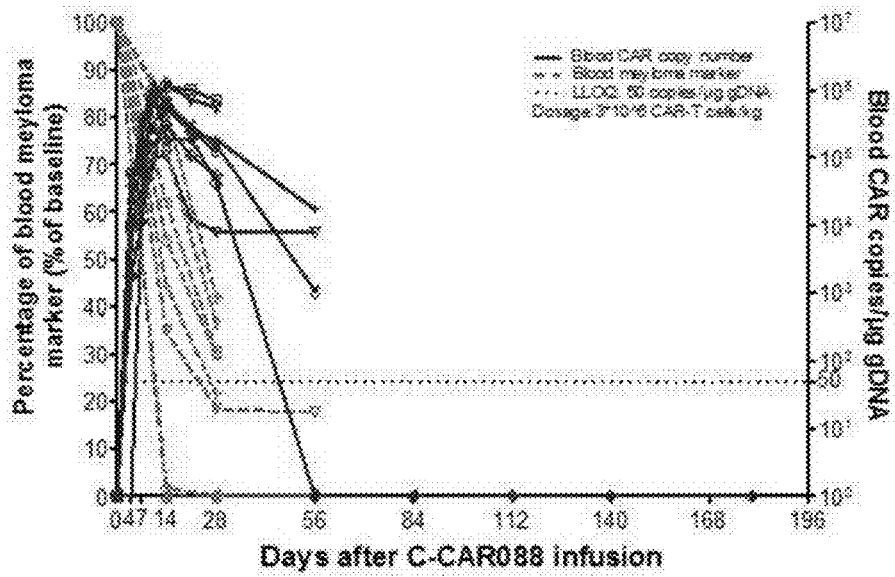
FIG. 17 shows the expansion of C-CAR008 and the decrease of M-protein/sFLC levels in the blood.

FIG. 17 shows the expansion of C-CAR008 and the decrease of M-protein/sFLC levels in the blood. The results showed that C-CAR008 cells expanded effectively after injection, and the level of M-protein/sFLC markers continued to decrease. The M-marker level of one patient was dropped to 0 on day 14.

Summary of observations for C-CAR088 was as follow.
In preclinical studies, C-CAR088 shows antitumor activity both in vitro and in vivo.
Early C-CAR088 trial results in patients with r/r MM support preclinical findings, show promising efficacy and manageable safety profile.
The early clinical efficacy signal at low, suboptimal dose is encouraging.
Compared to KarMMa data, our current dose level from infused patients is well below the optimal dose of bb2121. 53% (8/15) were recently dosed (at ~4 weeks). Given more time, it is possible that more patients could achieve CR over the natural course of M protein clearance.
Dose dependence is observed based on PK profile. C-CAR088 is well tolerated in patients, supporting continued optimal dose finding study. We will evaluate the therapeutic index of more patients at $6\times10^6$ CAR+ cell/kg dosing level.
It is essential to evaluate the duration of response (DOR) of C-CAR088 and actively seek approaches to improve the DOR.
CBMG's proprietary culture formulation and manufacturing process (4-5 days) could potentially add a competitive advantage over peer products.
All literatures mentioned in the present application are incorporated herein by reference, as though each one is individually incorporated by reference. In addition, it should also be understood that, after reading the above teachings of the present invention, those skilled in the art can make various changes or modifications, equivalents of which falls in the scope of claims as defined in the appended claims.

The invention claimed is:

1. A chimeric antigen receptor (CAR), comprising an anti-BCMA antigen binding region which comprises: (i) a light chain variable region ($V_L$) having an amino acid sequence set forth in SEQ ID NO: 1, and (ii) a heavy chain variable region ($V_H$) having an amino acid sequence set forth in SEQ ID NO: 2;
 wherein $V_L$ is located at the N-terminus of $V_H$,
 wherein the anti-BCMA antigen-binding region is a single-chain variable fragment (scFv) that specifically binds BCMA,
 wherein the CAR further comprises:
 (a) a signal peptide having an amino acid sequence set forth in SEQ ID NO: 9,
 (b) a hinge region having an amino acid sequence set forth in SEQ ID NO: 12,
 (c) a transmembrane domain having an amino acid sequence set forth in SEQ ID NO: 13,
 (d) a co-stimulatory region having an amino acid sequence set forth in SEQ ID NO: 14, and
 (e) a cytoplasmic signaling domain having an amino acid sequence set forth in SEQ ID NO: 15.

2. The CAR of claim 1, comprising from N-terminus to C-terminus: the signal peptide, $V_L$, $V_H$, the hinge region, the transmembrane domain, the co-stimulatory region, and the cytoplasmic signaling domain.

3. An engineered T cell expressing a chimeric antigen receptor (CAR), wherein the CAR comprises an anti-BCMA antigen binding region which comprises: (i) a light chain variable region ($V_L$) having an amino acid sequence set forth in SEQ ID NO: 1, and (ii) a heavy chain variable region ($V_H$) having an amino acid sequence set forth in SEQ ID NO: 2;
 wherein $V_L$ is located at the N-terminus of $V_H$,
 wherein the anti-BCMA antigen-binding region is a single-chain variable fragment (scFv) that specifically binds BCMA,
 wherein the CAR further comprises:
 (a) a signal peptide having an amino acid sequence set forth in SEQ ID NO: 9,
 (b) a hinge region having an amino acid sequence set forth in SEQ ID NO: 12,
 (c) a transmembrane domain having an amino acid sequence set forth in SEQ ID NO: 13,
 (d) a co-stimulatory region having an amino acid sequence set forth in SEQ ID NO: 14, and
 (e) a cytoplasmic signaling domain having an amino acid sequence set forth in SEQ ID NO: 15.

4. A pharmaceutical composition comprising an engineered T cell expressing a chimeric antigen receptor (CAR), wherein the CAR comprises an anti-BCMA antigen binding region which comprises: (i) a light chain variable region ($V_L$) having an amino acid sequence set forth in SEQ ID NO: 1, and (ii) a heavy chain variable region ($V_H$) having an amino acid sequence set forth in SEQ ID NO: 2;
 wherein $V_L$ is located at the N-terminus of $V_H$,
 wherein the anti-BCMA antigen-binding region is a single-chain variable fragment (scFv) that specifically binds BCMA,
 wherein the CAR further comprises:
 (a) a signal peptide having an amino acid sequence set forth in SEQ ID NO: 9, (b) a hinge region having an amino acid sequence set forth in SEQ ID NO: 12,
(c) a transmembrane domain having an amino acid sequence set forth in SEQ ID NO: 13,
(d) a co-stimulatory region having an amino acid sequence set forth in SEQ ID NO: 14, and
(e) a cytoplasmic signaling domain having an amino acid sequence set forth in SEQ ID NO: 15.

* * * * *

SEQUENCE LISTING

```
<160> NUMBER OF SEQ ID NOS: 15

<210> SEQ ID NO 1
<211> LENGTH: 107
<212> TYPE: PRT
<213> ORGANISM: Artificial Sequence
<220> FEATURE:
<223> OTHER INFORMATION: BCMA-20 light chain variable region

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Asn Trp Tyr Gln Gln Lys Pro Gly Lys Ala Pro Lys Pro Leu Ile
        35                  40                  45

Tyr Tyr Thr Ser Asn Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Met Gly Gln Thr Ile Ser Ser Tyr
                85                  90                  95

Thr Phe Gly Gln Gly Thr Lys Leu Glu Ile Lys
            100                 105

<210> SEQ ID NO 2
<211> LENGTH: 121
<212> TYPE: PRT
<213> ORGANISM: Artificial Sequence
<220> FEATURE:
```

<223> OTHER INFORMATION: BCMA-20 heavy chain variable region

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Phe
            20                  25                  30

Asp Met Ala Trp Val Arg Gln Ala Pro Gly Lys Gly Leu Val Trp Val
        35                  40                  45

Ser Ser Ile Thr Thr Gly Ala Asp His Ala Ile Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg His Gly Tyr Tyr Asp Gly Tyr His Leu Phe Asp Tyr Trp Gly
            100                 105                 110

Gln Gly Thr Leu Val Thr Val Ser Ser
            115                 120

<210> SEQ ID NO 3
<211> LENGTH: 108
<212> TYPE: PRT
<213> ORGANISM: Artificial Sequence
<220> FEATURE:
<223> OTHER INFORMATION: BCMA-CA8 light chain variable region

<400> SEQUENCE: 3

Asp Ile Gln Leu Thr Gln Thr Thr Ser Ser Leu Ser Ala Ser Leu Gly
1               5                   10                  15

Asp Arg Val Thr Ile Ser Cys Ser Ala Ser Thr Thr Ser Asn Tyr
            20                  25                  30

Leu Asn Trp Tyr Gln Gln Lys Pro Asp Gly Thr Val Glu Leu Val Ile
        35                  40                  45

Tyr Tyr Thr Ser Asn Leu His Gly Gly Gly Pro Ser Arg Phe Ser Gly
    50                  55                  60

Ser Gly Ser Gly Thr Asp Tyr Ser Leu Thr Ile Gly Tyr Leu Glu Pro
65                  70                  75                  80

Glu Asp Val Ala Thr Tyr Tyr Cys Gln Gln Tyr Arg Lys Leu Pro Trp
                85                  90                  95

Thr Phe Gly Gly Gly Ser Lys Leu Glu Ile Lys Arg
            100                 105

<210> SEQ ID NO 4
<211> LENGTH: 121
<212> TYPE: PRT
<213> ORGANISM: Artificial Sequence
<220> FEATURE:
<223> OTHER INFORMATION: BCMA-CA8 heavy chain variable region

<400> SEQUENCE: 4

Glu Val Gln Leu Gln Gln Ser Gly Ala Val Leu Ala Arg Pro Gly Ala
1               5                   10                  15

Ser Val Lys Met Ser Cys Lys Gly Ser Gly Tyr Thr Phe Thr Asn Tyr
            20                  25                  30

Trp Met His Trp Val Lys Gln Arg Pro Gly Gln Gly Leu Glu Trp Ile
        35                  40                  45

Gly Ala Thr Tyr Arg Gly His Ser Asp Thr Tyr Tyr Asn Gln Lys Phe

```
                    50                  55                  60
Lys Gly Lys Ala Lys Leu Thr Ala Val Thr Ser Thr Ser Thr Ala Tyr
 65                  70                  75                  80

Met Glu Leu Ser Ser Leu Thr Asn Glu Asp Ser Ala Val Tyr Tyr Cys
                     85                  90                  95

Thr Arg Gly Ala Ile Tyr Asn Gly Tyr Asp Val Leu Asp Asn Trp Gly
                    100                 105                 110

Gln Gly Thr Leu Val Thr Val Ser Ser
                115                 120

<210> SEQ ID NO 5
<211> LENGTH: 108
<212> TYPE: PRT
<213> ORGANISM: Artificial Sequence
<220> FEATURE:
<223> OTHER INFORMATION: BCMA-M06 light chain variable region

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Leu Leu Ile
             35                  40                  45

Tyr Tyr Thr Ser Asn Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Arg Lys Leu Pro Trp
                 85                  90                  95

Thr Phe Gly Gln Gly Thr Lys Leu Glu Ile Lys Arg
                100                 105

<210> SEQ ID NO 6
<211> LENGTH: 121
<212> TYPE: PRT
<213> ORGANISM: Artificial Sequence
<220> FEATURE:
<223> OTHER INFORMATION: BCMA-M06 heavy chain variable region

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Asn Tyr
                20                  25                  30

Trp Met His Trp Val Arg Gln Ala Pro Gly Gln Gly Leu Glu Trp Met
             35                  40                  45

Gly Ala Thr Tyr Arg Gly His Ser Asp Thr Tyr Tyr Asn Gln Lys Phe
 50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Ala Ile Tyr Asp Gly Tyr Asp Val Leu Asp Asn Trp Gly
                100                 105                 110

Gln Gly Thr Leu Val Thr Val Ser Ser
                115                 120
```

<210> SEQ ID NO 7
<211> LENGTH: 111
<212> TYPE: PRT
<213> ORGANISM: Artificial Sequence
<220> FEATURE:
<223> OTHER INFORMATION: BCMA-1 light chain variable region

<400> SEQUENCE: 7

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Glu Asp Asp Val Ala Val Tyr Tyr Cys Leu Gln Ser Arg
                85                  90                  95

Thr Ile Pro Arg Thr Phe Gly Gly Gly Thr Lys Leu Glu Ile Lys
            100                 105                 110

<210> SEQ ID NO 8
<211> LENGTH: 117
<212> TYPE: PRT
<213> ORGANISM: Artificial Sequence
<220> FEATURE:
<223> OTHER INFORMATION: BCMA-1 heavy chain variable region

<400> SEQUENCE: 8

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115

<210> SEQ ID NO 9
<211> LENGTH: 21
<212> TYPE: PRT
<213> ORGANISM: Artificial Sequence
<220> FEATURE:
<223> OTHER INFORMATION: CD8 Signal peptide

<400> SEQUENCE: 9

Met Ala Leu Pro Val Thr Ala Leu Leu Leu Pro Leu Ala Leu Leu Leu
1               5                   10                  15

His Ala Ala Arg Pro

-continued

```
<210> SEQ ID NO 10
<211> LENGTH: 18
<212> TYPE: PRT
<213> ORGANISM: Artificial Sequence
<220> FEATURE:
<223> OTHER INFORMATION: linker

<400> SEQUENCE: 10

Gly Ser Thr Ser Gly Ser Gly Lys Pro Gly Ser Gly Glu Gly Ser Thr
1               5                   10                  15

Lys Gly

<210> SEQ ID NO 11
<211> LENGTH: 15
<212> TYPE: PRT
<213> ORGANISM: Artificial Sequence
<220> FEATURE:
<223> OTHER INFORMATION: linker

<400> SEQUENCE: 11

Gly Gly Gly Gly Ser Gly Gly Gly Gly Ser Gly Gly Gly Gly Ser
1               5                   10                  15

<210> SEQ ID NO 12
<211> LENGTH: 55
<212> TYPE: PRT
<213> ORGANISM: Artificial Sequence
<220> FEATURE:
<223> OTHER INFORMATION: Hinge

<400> SEQUENCE: 12

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp
    50                  55

<210> SEQ ID NO 13
<211> LENGTH: 24
<212> TYPE: PRT
<213> ORGANISM: Artificial Sequence
<220> FEATURE:
<223> OTHER INFORMATION: CD8 transmembrane domain

<400> SEQUENCE: 13

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 14
<211> LENGTH: 42
<212> TYPE: PRT
<213> ORGANISM: Artificial Sequence
<220> FEATURE:
<223> OTHER INFORMATION: 4-1BB Costimulatory sequence

<400> SEQUENCE: 14

Lys Arg Gly Arg Lys Lys Leu Leu Tyr Ile Phe Lys Gln Pro Phe Met
```

```
1               5                   10                  15
Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 15
<211> LENGTH: 113
<212> TYPE: PRT
<213> ORGANISM: Artificial Sequence
<220> FEATURE:
<223> OTHER INFORMATION: CD3 zeta

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```